United States Patent [19]

Nagata et al.

[11] Patent Number: 5,266,491
[45] Date of Patent: Nov. 30, 1993

[54] DNA FRAGMENT AND EXPRESSION PLASMID CONTAINING THE DNA FRAGMENT

[75] Inventors: Shigekazu Nagata, Suita; Seiichi Mizushima, Tokyo, both of Japan

[73] Assignee: Mochida Pharmaceutical Co., Ltd., Tokyo, Japan

[21] Appl. No.: 757,536

[22] Filed: Sep. 11, 1991

Related U.S. Application Data

[63] Continuation-in-part of Ser. No. 447,823, Dec. 8, 1989.

[30] Foreign Application Priority Data

Mar. 14, 1989 [JP] Japan .................................. 1-61702

[51] Int. Cl.$^5$ ...................... C12N 15/11; C12N 15/67; C12N 15/79; C07H 21/04
[52] U.S. Cl. ................. 435/320.1; 536/24.1; 935/6; 935/24; 935/34
[58] Field of Search ................. 536/27; 935/6, 22, 24, 935/34; 435/320.1

[56] References Cited

PUBLICATIONS

Yakov Gluzman, Cell, vol. 23, pp. 175–182, Jan. 1981.
Seiichi Mizushima and Shigekazu Nagata (1990), Nucleic Acids Research, vol. 18, No. 17, p. 5322.

*Primary Examiner*—George C. Elliott
*Attorney, Agent, or Firm*—Burns, Doane, Swecker & Mathis

[57] ABSTRACT

Novel expression plasmids containing SV40 replication origin and a DNA fragment having a promoter region for a human polypeptide chain elongation factor-1α gene.

The expression plasmids have high applicability to a wide range of host cells with high expression efficiency in transient expression systems.

7 Claims, 21 Drawing Sheets

Fig. 1-1

```
1                                                          60              Met Gly Lys Glu Lys Thr His Ile Asn Ile
TTTTCGAACGGGTTTGCCGGCCAGAACACAGGTGTCGTGAAAACTACCCCTAAAAGCCAAA ATG GGA AAG GAA AAG ACT CAT ATC AAC ATT
                                                                                              80
Val Val Gly His Val Asp Ser Gly Lys Ser Thr Thr Thr Gly His Leu Ile Tyr Lys Cys Gly Gly Ile Asp Lys Arg Thr Ile Glu
GTC GTT GGA CAC GTA GAT TCG GGC AAG TCC ACC ACT ACT GGC CAT CTG ATC TAT AAA TGC GGT GGT ATC GAC AAA AGA ACC ATT GAA
100                               120                               140                              160              180
Lys Phe Glu Lys Glu Met Gly Lys Gly Ser Phe Lys Tyr Ala Trp Val Leu Asp Lys Leu Lys Ala Glu Arg Glu Arg Gly
AAA TTT GAG AAG GAG ATG GGA AAG GGA TCC TTC AAG TAT GCC TGG GTC TTG GAT AAA CTG AAA GCT GAG CGT GAA CGT GGT
                    200                              220                              240                              260
Ile Thr Ile Asp Ile Ser Leu Trp Lys Phe Glu Thr Ser Lys Tyr Tyr Val Thr Ile Ile Asp Ala Pro Gly His Arg Asp Phe Ile Lys
ATC ACC ATT GAT ATC TCC TTG TGG AAA TTT GAG ACA AGC ACC AGT AAG TAC TAT GTG ACT ATT ATC GAT GCC CCA GGA CAC AGA GAC TTT ATC AAA
   280                              300                              320                              340                      360
Asn Met Ile Thr Gly Thr Ser Gln Ala Asp Cys Ala Val Leu Val Gly Val Ala Ala Gly Val Gly Phe Glu Ala Gly Ile Ser Lys Asn
AAC ATG ATT ACA GGG ACA TCT CAG GCT GAC TGT GCT GTC CTG GTT GGT GTT GCT GCT GGT GTG GGT TTT GAA GCT GGT ATC TCC AAG AAT
            380                              400                              420                              440
Gly Gln Thr Arg Glu His Ala Leu Leu Ala Tyr Thr Leu Gly Val Lys Gln Asn Lys Val Val Gly Ile Val Leu Gln Met Asp Ser Thr Arg Glu Pro
GGG CAG ACC CGA GAG CAT GCC CTT CTG GCT TAC ACA CTA GGT GTG AAA CAA AAC AAG GTC ATT GTC ATA CTA CAA ATG GAT TCC ACT GAG CCA
    460                              480                              500                              520                        540
Pro Tyr Ser Gln Lys Arg Tyr Glu Glu Ile Val Lys Glu Val Ser Thr Tyr Ile Lys Lys Ile Gly Tyr Asn Pro Asp Thr Val Ala Phe
CCC TAC AGC CAG AAG AGA TAT GAG GAA ATT GTT AAG GAA GTC AGC ACT TAC ATT AAG AAA ATT GGC TAC AAC CCC GAC ACA GTA GCA TTT
              560                              580                              600                              620                   720
Val Pro Ile Ser Gly Trp Asn Gly Asp Asn Met Leu Glu Pro Ser Ala Asn Met Pro Trp Phe Lys Gly Trp Lys Val Thr Arg Lys Asp
GTG CCA ATT TCT GGT TGG AAT GGT GAC AAC ATG CTG GAG CCA AGT GCT AAC ATG CCT TGG TTC AAG GGA TGG AAA GTC ACC CGT AAG GAT
        640                              660                              680                              700
Gly Asn Ala Ser Gly Thr Thr Leu Leu Glu Ala Leu Asp Cys Ile Leu Pro Pro Thr Arg Pro Thr Asp Lys Pro Leu Arg Leu Pro Leu
GGC AAT GCC AGT GGA ACC ACG CTT CTT GAG GCT CTG GAC TGC ATC CTA CCA CCA ACT CGT CCA ACT GAC AAG CCC CTG CGC CTG CCT CTC
                          740                              760                              780                              800
```

Fig. 1-2

```
                                        860                                           880                               900
     820                         840            Arg Val Gly Thr Val Pro Val Glu Thr Gly Val Leu Lys Pro Gly Met Val Val Thr Phe
Gln Asp Tyr Lys Ile Gly Gly Thr Val Gly Ile          GTT GGC ACT GTT CCT GTT GAG ACT GGT GTT CTC AAA CCC GGT ATG GTG GTC ACC TTT
CAG GAT TAC AAA ATT GGT GGT ACT GTT GGT ATT     CGA
                                                                      960                            980
                           920                        940
                                                                 Glu Ala Leu Pro Gly Met Asp Asn Val Gly Phe
Ala Pro Val Asn Val Thr Thr Glu Thr Val Lys Ser Val Met Glu His                                                           1080
                                                 ATG GAA CAT GAA GCT CTT CCT GGG GAC AAT GTG GGC TTC
GCT CCA GTC AAC GTT ACA ACG GAA ACG GTA AAA TCT GTC
                                                                 1040                                 1060
     1000                           1020
                                                      Gly Asp Ser Lys Asn Asp Pro Pro Met Glu Ala Ala Ala Gly Phe
Asn Val Lys Asn Val Ser Val Asp Arg Val Lys Arg                                                                   1160
                                                 GGT GAC AGC AAA AAT GAC CCA CCA ATG GAA GCA GCT GGC TTC
AAT GTC AAG AAT GTG TCT GTC GAT CGT GTT AAG CGT
                                                                                                      1140                    Ile Ala His Thr Ala Ala Cys
                                                      Ser Ala Gly Tyr Ala Pro Val Leu Asp Cys His
     1060                           1120                                                         ATT CAC ACG GCT GCA TGC
                                                                 AGC GCC TAT GCC CCT GTA TTG GAT TGC
Thr Ala Gln Val Ile Ile Leu Asn His Pro Gly Gln
                                                                                                      1240                                 1260
ACT GCT CAG GTG ATT ATC CTG AAC CAT CCA GGC CAA              1220
                                                                                                            Leu Lys Ser Asp Ala Ala
                                                      Lys Arg Arg Ser Gly Lys Phe Leu Arg Lys         Gly
                           1180                                                                           TGG AAG TCT GAT GCT GCC
                                                                 AAA AGG CGC TCT GGT AAA TTC CTT TTG
Lys Phe Ala Glu Leu Lys Glu Lys Ile Asp Arg                                                                          1340
                                                                                                      1320
AAG TTT GCT GAG CTG AAG GAA AAG ATT GAT CGC                           1300                                                      Arg Phe Ala Arg Met
                                                                                                      Tyr Pro Pro Lys Leu Gly Arg
                                                                 Val Glu Ser Phe Ser Asp                                    TTT GCT CGT GAT ATG
     1180                                             Met Cys
                                                                 GTT GAG AGC TTC TCA GAC TAT CCA CCT AAG TTG GGT CGC
Ile Val Asp Met Val Gly Lys Pro Gly                   ATG TGT
ATT GTT GAT ATG GTT GGT CCT                                                                                                        1420
                                                                                                      Val Thr Ser Ala Gln Lys Ala Gln
                                                                 Ala Val Ile Lys Ala Gly Val Ala
     1280                                             Ile                                                   GTC ACC TCT GCC CAG AAA GCT CAG
                                                                 GCA GTG ATC AAA GCG GGT GTG GCT
                           1360                       ATA                                                               1540
Arg Gln Thr Val Ala Val                               Ala                                             1500                              1520
AGA CAG ACA GTT GCG         1480
                                                                              CCCCACTCTTAATCAGTGGTGGAAGAACGGTCTCAGAACTGTTTGTTTCAATTGGCCATTAAGTTAGTAGTAAAAGACT
     Lys Ala Lys End        1460      ATATTATCCCTAATACCTGCCACCCACTCTTAATCAGTGGTGGAAGAACGGTCTCAGAACTGTTTGTTTCAATTGGCCATTAAGTTAGTAGTAAAAGACT
     AAG GCT AAA TGA                                                                                  1640                                       1660
                                                 1580                                 1620
                                      GGTTAATGATAACAATGCATGTAAAACCTTCAGAAGGAAAGGAGAATGTTTGTGGACCACTTGGTTTTCTTTTTTGCGTGTGGCAGTTTAAGTTATTAGTTTTTAAAATCAGTAC
                 1560
                           1680                                                      1740
                                                 1700
                                      TTTTTAA TGGAAACAACTTGACCAAAAATTTGTCACAGAATTTTGAGACCCATTAAAAAAGTTAAATGAGAAAAAAAA
```

Fig. 3-1

```
                                20                      40                      60                      80                     100
CCCGGGGCTGGGCTGAGAGACCCGCAGAGGAAGACGCGCTCTAGGGATTTGTCCCGGACTAGCGAGGATGGGCGAAGGCTGAGAGCTGAGAGGCGAAGGTACACCCTAATCTCAAT
                               140                     160                     180                     200                     220
ACAACCCTTTGGAGCTAAGCCAGCAATGGTAGAGGGAAGATTCTGCACGTCCCTTCCAGGCGGCCTCCCGTCACCACCCCGCCCAACCCGACCGGAGCTGAGAGTAATTCATAC
                               260                     280                     300                     320                     340
AAAAGGACTCGCCCCTGCCTTGGGGAATCCCACTAACGTCGTTAAACTCCCACTAGAACCCAGAGATCGCTGCGTTCCCGCGCCCCCTCACCCGCCCGGCTCTCGTCATCACTGAG
                               380                     400                     420                     440                     460
GTGGAGAAGAGCATGCGTGAGGCTCCGGTGCCCGTCAGTGGGCAGAGCGCACATCGCCAGTCCCCGAGAAGTTGGGCGGCAATTGAACCGGTGCCTAGAGAAGGTGG
                               500                     520                     540                     560                     * exon 1
CGCGGGGTAAACTGGGAAAGTGATGTCGTACTGGGCTCCGCTCCCGAGGGTGGGGGAGAACGTATATAAGTGCAGTAGTCGCCGTGAACGTTCTTTTTCGCAACGGGTTTGC
                600                     640                     660                     680                     700
intron 1
CGCCAGAACACAG GTAAGTGCCGTGTCGTGTGTGAGGCCCTCTTTGCGTGCCTTGAATTACTTCCACGCCCCCTGGCTGCAGTACGTGATTCTTGA
                740                     760                     780                     800                     820
TCCCGAGCTTCGGGTTGGAAGTGGGGTGGGAGAGTTCGAGGTTCGGCCTTAAGGAGCCCCTTGCGCTTGAGTTGAGGCCTCGTGCCTGGAGCCGCGGTGCCAATCT
                860                     880                     900                     920                     940
GGTGGCACCTTCGCCGCTGTCTCGCTGCTTCGCTAGCCATTTAAATTTTTGATGAAGTCTCTAGCCATTTAAATTTTTGATGACCTGCTGCCGACGCTTGTAAATGCGGGCCAAGAT
                980                     1000                    1020                    1040                    1060
CTGCACACTGGATTTCGGTTTTGGGGCCGGGCCTGGCCTTGGACGGGAGCGGCCCGTGCCGTCCCAGCGACGCGGGCCTGCGAGCGCCACCGAGAATCGGACGGGGGTA
                1100                    1120                    1140                    1160                    1180
GTCTCAAGCTGGCCTGCCTGCTGCGCCGCGGCCCGTGTATCGGCCGCGGCCAAGGCTGGGCGGCACCAGTTGCGTGAGCGGGAAAGATGGCCGCTC
                1220                    1240                    1260                    1280                    1300
CCGGGCCCTGCTCAGGAGGCGCCGTCAAAATGGAGGAGACGCGGACGCGGGCGGGCGAGTGAGTGGGTGAGTCACCCACACACAAAGGAAAAGGGGCCTTTCCGTCGCTTCATGTGACTCC
                1340                    1360                    1380                    1400                    1420
ACGGAGTACCGGGGCGCCGCCCAGGCACCTCGAGCTGATTAGTTCTCGAGCTTTTGGAGTACGTCGTCTTTATGCGATGGAGTTTCCCACACTGAGTGGGTGGA
                1440                    1460                    1480                    1500                    1520
GACTGAAGTTAGGCCAGCTTGGCACTTGATGTAATTGCCCTTTTTGCCCTTTTTGGAATTTGCCCTTTTGCATCTCAAGCCTGGTTCAAGCTGGTTCAAAGTTTTTTCTTCCAT
                1580                    1600                    1620                    1640
exon 2
TTCAG GTGTCGTGAAAACTACCCCTAAAAGCCAAA ATG GGA AAG GAA AAG ACT CAT ATC AAC ATT GTC ATT GGA CAC GTA GAT TCG GCT GAG AAG
                                                                Met Gly Lys Glu Lys Thr His Ile Asn Ile Val Ile Gly His Val Asp Ser Ala Glu Lys
                                                                 1                        10                              20
                                                     1680                                    1700                                   1720
TCC ACT ACT GGC CAT CTG ATC TAT AAA TGC GGT GGC ATC GAC AAA AGA ACC ATT GAA AAA TTT GAG AAG GAG GCT GAG GTATGTT
Ser Thr Thr Gly His Leu Ile Tyr Lys Cys Gly Gly Ile Asp Lys Arg Thr Ile Glu Lys Phe Glu Lys Glu Ala Glu
                        30                              40
```

```
                                                                            exon 6                                                                                              3040
             2960                     2980                                                         3020
GTCTGCCTTCATAGGTATTTAGTATGCTGTAAATATTTTAG GT ATT GGT ACT GTT CCT GTT GGC CGA GTG GAG ACT GGT GTT CTC AAA CCC GGT ATG
                                                                Ly Ile Gly Thr Val Pro Val Gly Arg Val Glu Thr Gly Val Leu Lys Pro Gly Met
                                                                           260                       270
             3060                    3080                    3100                    3120                                             3140
GTG GTC ACC TTT GCT CCA GTC AAC GTT ACA ACG GAA GTA AAA TCT GTC GAA ATG CAC CAT GAA GCT TTG AGT GAA GCT CTT CCT GGG GAC
Val Val Thr Phe Ala Pro Val Asn Val Thr Thr Glu Val Lys Ser Val Glu Met His His Glu Ala Leu Ser Glu Ala Leu Pro Gly Asp
                 280                                 290                                 300
                                                                                                                        3220
             3160                    3180                    3200                                                                                                 3340
AAT GTG GGC TTC AAT GTC AAG AAT GTG TCT GTC AAG GAT GTT CGT CGT GGC AAC GTT GCT GGT GAC AGC AAA AAT GAC CCA CCA ATG GAA
Asn Val Gly Phe Asn Val Lys Asn Val Ser Val Lys Asp Val Arg Arg Gly Asn Val Ala Gly Asp Ser Lys Asn Asp Pro Pro Met Glu
                 310                                 320                                 330
                                                             intron 6                                 3300
             3240
GCA GCT GGC TTC ACT GCT CAG GTAACAATTTAAAGTAACATTAACTTATTGCAGAGGCTAAAGTCATTTGAGACTTTGGATTTGCACTGAATGCAAATCTTTTTCCAAG
Ala Ala Gly Phe Thr Ala Gln
             340
                                                                                                                                        3420
    exon 7                                             3380                                 3400                                                                              3520
             3360                                                                                                                                     TGC AAG TTT GCT
GTG ATT ATC CTG AAC CAT CCA GGC CAA ATA AGC GCC GGC TAT GCC CCT GTA TTG GAT TGC CAC ACG GCT CAC ATT GCA CAT
Val Ile Ile Leu Asn His Pro Gly Gln Ile Ser Ala Gly Tyr Ala Pro Val Leu Asp Cys His Thr Ala His Ile Ala Cys Lys Phe Ala
                 350                                 360                                                                        370
                                                                                                                        3500                    3520
             3440                    3460                    3480
GAG CTG AAG GAA AAG ATT GAT CGC CGT TCT GGT AAA AAG CTG GAA GAT GGC CCT AAA TTC TTG AAG TCT GGT GAT GCC ATT GTT GAT
Glu Leu Lys Glu Lys Ile Asp Arg Arg Ser Gly Lys Lys Leu Glu Asp Gly Pro Lys Phe Leu Lys Ser Gly Asp Ala Ile Val Asp
                 380                                 390                                 400
                                                                    intron 7                                                                                      3620
             3540                    3560                                                 3600
ATG GTT CCT GGC AAG CCC ATG TGT GTT GAG AGC TTC TCA GAC TAT CCA CCT TTG G GTAAGGATGACTACTTAAATGTAAAAAGTTGTGTTAAAGATGAA
Met Val Pro Gly Lys Pro Met Cys Val Glu Ser Phe Ser Asp Tyr Pro Pro Leu G
                 410                                 420
                                                            exon 8                                             3700                    3720
             3640                    3660                    3680                                                                                                 3800
AAATACAACTGAACAGTACTTTGGGTAATAATTAACTTTTTTTTAATAG GT CGC TTT GCT CGT GAT ATG AGA CAG ACA GTT GCG GTG GGT GTC ATC
                                                    Ly Arg Phe Ala Val Arg Asp Met Arg Gln Thr Val Ala Val Gly Val Ile
                                                                430
                                                                                 3780                                 3800
             3740                    3760
AAA GCA GTG GAC AAG AAG GCT GGA GCT GGC AAG TCT GCC ACC AAG GTC AAG AAA GCT CAG AAG GCT AAA TGA ATATTATCCCTAATACCTG
Lys Ala Val Asp Lys Lys Ala Gly Ala Gly Lys Ser Ala Thr Lys Val Lys Lys Ala Gln Lys Ala Lys End
                 440                                 450                                 460
                                                                                                                                                  3920
             3820                    3840                    3860                    3880
CCACCCCACTCTTAATCAGTGGTGGAAGAACGGTCTCAGAACTGTTGTTTCAATTGGCCATTTAAGTTAGTAGTAAAGACTGGTTAATGATAACAATGCATCGTAAACCTTCAGA
```

Fig. 3-4

```
      3940         3960         3980         4000         4020         4040
AGGAAAGGAGAATGTTTTGTGGACCACTTTGGGTTTTCTTTTTTGCGTGTGGCAGTTTTAAGTTATTAGTTTTTAAAATCAGTACTTTTAATGGAAACAACTTGACCAAAAATTGTCA
      4060         4080         4100         4120         4140         4160
CAGAATTTTGAGACCCATTAAAAAAGTTAAATGAGAAACCTGTGTGTTCCTTTGGTCAACACCGAGACATTTAGGTGAAAGACATCTAATTCTGGTTTTACGAATCTGGAAACTTCTTG
      4180         4200         4220         4240         4260         4280
AAAATGTAATTCTTGAGTTAACACTTCTGGGTGGAGAATAGGGTTGTTTTCCCCCCACATAATTGGAAGGGGAAGGAATATCATTAAAGCTATGGGAGGGTTCTTTGATTACAACAC
      4300         4320         4340         4360         4380         4400
TGGAGAGAAATGCAGCATGTTGCTGATTGCCTGTCACTAAAACAGGCCAAAAACTGAGTCCTTGGGTTGCATAGAAAGCTTCATGTTGCTAAACCAATGTTAAGTGAATCTTTGGAAAC
      4420         4440         4460         4480         4500         4520
AAAATGTTTCCAAATTACTGGAATGTGCATGTTGAAACGTGGGTTAAAATGACTGGGCAGTGAAAGTTGACTATTGCCATGACATAAGAAATAAGTGTAGTGGCTAGTGTACACCCTA
      4540         4560         4580         4600         4620         4640
TGAGTGGAAGGGTCCATTTTGAAGTCAGTGGAGTAAGCTTTATGCCATTTGATGGTTTCACAAGTTCTATTGAGTGCTATTCAGAATAGGAACAAGGTTCTAATAGAAAAAGATGGCA
      4660         4680
ATTTGAAGTAGCTATAAAAATTAGACTAATTACATTGCTTTTCTCCGAC
```

— indicates human EF-1α chromosomal gene.
☐ indicates exons in human EF-1α chromosomal gene (Exons are numbered consecutively.)

— indicates human EF-1α chromosomal gene.
| indicates exons in human EF-1α chromosomal gene.
(Exons are numbered consecutively.)

— indicates human EF-1α chromosomal gene.

| indicates exons in human EF-1α chromosomal gene.
(Exons are numbered consecutively.)

▭ indicates CAT gene.

( ) indicates eliminated restriction enzyme recognition region.

Fig. 10

|  | pEF204 -CAT | pEF220 -CAT | pEF223 -CAT | pEF321 -CAT | pSV2 -CAT | pSR2 -CAT |
|---|---|---|---|---|---|---|
| 3',1''-DIACETYLCHLORAMPHENICOL | 498 | 159 | 541 | 474 | 6 | 57 |
| 3'-ACETYLCHLORAMPHENICOL | | | | | | |
| 1''-ACETYLCHLORAMPHENICOL | | | | | | |
| CHLORAMPHENICOL | 25 | 366 | 26 | 17 | 572 | 595 |

DNA FRAGMENT AND EXPRESSION PLASMID CONTAINING THE DNA FRAGMENT

REFERENCE TO RELATED APPLICATION

This application is a continuation-in-part of U.S. application Ser. No. 07/447,823, filed Dec. 8, 1989, herein incorporated by reference.

BACKGROUND OF THE INVENTION

This invention relates to a novel DNA fragment having an active promoter region and some expression plasmids containing said DNA fragment, both of which are effective for use in the production of physiologically active substances by means of recombinant DNA technology. In particular, this invention relates to a novel DNA fragment having the promoter region of a human polypeptide chain elongation factor gene and some expression plasmids containing said DNA fragment.

With the advance of gene engineering studies, production of substances by recombinant DNA technology has come into a common means. Methods have been established almost completely for the production of foreign proteins by means of recombinant DNA technology using *E. coli* as the host. The use of *E. coli*, however, is still inappropriate for the production of a protein which essentially requires the addition of sugar chains or a protein whose physiological activity or antigenicity is altered when it is produced in a different cell type.

For the purpose of solving such a problem, various host systems have been developed using animal cells. In general, three signals are required for the gene expression in animal cells; that is, promoter, RNA splicing signal and poly (A) addition signal. It is important to select an efficient promoter for a high level expression of the gene for a protein of interest. Promoters which are being used commonly include the SV40 (a papovavirus) early promoter, adenovirus major late promoter and metallothionein promoter originated from mouse and the like. The SV40 early promoter is being used most frequently, but this promoter still has the disadvantage of low level expression capacity and narrow host range. In other words, tissue-specific expression and cell type-dependent changes in the level of expression capacity are unavoidable even if the SV40 early promoter is used. For example, the expression capacity is remarkably low in lymphoid cells and nerve cells compared to other cell types.

Recently, Y. Takebe et al. (*Mol. Cell. Biol.* 8:466; 1988) have constructed an SRα promoter by incorporating a portion of the terminal repeat sequence of human T-cell leukemia virus type 1 into downstream of the SV40 early promoter. According to the report, expression of the downstream gene of the SRα promoter was 1 or 2 orders of magnitude more active than that of the SV40 early promoter when a certain lymphoid cell was used as the host. However, it is still unclear whether the SRα promoter can maintain its high expression capacity in other host cells. If the diversity of useful physiologically active substances which will be produced in the future by means of recombinant DNA technology is taken into consideration, it is necessary to obtain a new promoter that has high level of expression capacity in more wider range of host cells and to develop an expression plasmid containing such a promoter.

A transient expression system, especially one in which simian COS cells are used (Gluzman, Y. 1981) *Cell* 23:175), is commonly employed when an attempt is made to clone a new gene by means of a biological assay using its activity as a marker. Such a transient expression system has an advantage in that a protein of interest can be obtained easily within a short period of time for use in the analysis of function and structure of the expressed protein. However, disadvantageously few expression plasmids are available for use in a transient expression system from which an expressed product can be obtained in a sufficiently large amount that the product can be detected, even by a low sensitivity biological assay system. Furthermore, until the present invention very little actually was known about an expression plasmid which could provide high expression efficiency in a broad range of host cells.

SUMMARY OF THE INVENTION

Taking the above-described situation of the prior art into consideration, the present inventors have performed studies on the screening of a novel DNA fragment containing a promoter region which could show high expression capacity in a wide range of host cells and on the development of an expression plasmid containing said DNA fragment. Through these studies, the present inventors have isolated a chromosomal gene encoding human polypeptide chain elongation factor-1α (to be referred to as human EF-1α hereinafter) which is constitutively produced in all human cells and have revealed structure of said gene by determining its base sequence.

Some expression plasmids were then constructed using a novel DNA sequence containing a promoter region for said gene. These expression plasmids were found to be efficiently applicable to a wider range of host cells with higher expression capacity than commonly used expression plasmids. The present invention has been accomplished as a result of these efforts.

Furthermore, the present inventors have found for the first time that novel expression plasmids containing a human EF-1α promoter region and a simian virus 40 (SV40) replication origin show high expression efficiency in a broad range of host cells in transient expression systems. Thus, the expression levels of the present invention has proven highly advantageous when compared with prior art expression plasmids.

Polypeptide chain elongation factors are enzymes which take part in the polypeptide chain elongation reaction in the translation process, and are classified into two groups in terms of their respective functions; that is, one factor catalyzes binding of aminoacyl-tRNA to the A site of a ribosome and the other factor transfers peptidyl-tRNA from the A site to the P site of a ribosome.

In the case of procaryotic cells, the above-described two kinds of polypeptide chain elongation factor (to be referred to as EF hereinafter) are called EF-T and EF-G, respectively, and the EF-T is divided further into EF-TU and EF-TS. In eucaryotic organisms, on the other hand, different EFs are independently located in the cytoplasm and the mitochondria. As a cytoplasmic EF, EF-1α whose function is equivalent to that of EF-Tu in *E. coli* has been found and purified from various cells and tissues of yeast, pig liver and the like.

The primary structure of human EF-1α cDNA has been determined by J. H. G. M. Brands et al. (*Eur. J. Biochem.* 155:167; 1986). However, the DNA sequence of the chromosomal gene has not been revealed, because, as will be described later, isolation of human EF-1α chromosomal gene was difficult to achieve due to the presence of many human EF-1α pseudogenes in the chromosome genes. As described above, the present inventors have isolated a human EF-1α chromosome gene, determined its base sequence and revealed for the first time a novel DNA sequence containing a promoter region of the human EF-1α gene and the DNA sequence of introns. Further, the inventors have found that the novel DNA fragment containing said promoter region stimulated the expression of its downstream gene. Therefore, the inventors have constructed a high expression plasmid containing said DNA fragment.

The first aspect of the present invention provides a novel DNA fragment containing a promoter region for a human polypeptide chain elongation factor gene.

The second aspect of the present invention provides an expression plasmid constructed by using a novel DNA fragment containing a promoter region of the human polypeptide chain elongation factor gene.

Preferably, the human polypeptide chain elongation factor gene may be the human polypeptide chain elongation factor-1α gene.

The present invention provides a novel DNA fragment comprising at least a portion or a whole of a region of about 2.5 kilo base pairs which is located immediately upstream of the initiation codon of the human polypeptide chain elongation factor gene.

The novel DNA fragment preferably contains a promoter region for human polypeptide chain elongation factor-1α gene, which is represented by the following sequence (SEQ ID No:1):

| Sequence | Position |
|---|---|
| CCCGGGCTGGGCTGAGACCCGCAGAGGAAGACGCTCTAGG | 40 |
| GATTTGTCCCGGACTAGCGAGATGGCAAGGCTGAGGACGG | 80 |
| GAGGCTGATTGAGAGGCGAAGGTACACCCTAATCTCAATA | 120 |
| CAACCTTTGGAGCTAAGCCAGCAATGGTAGAGGGAAGATT | 160 |
| CTGCACGTCCCTTCCAGGCGGCCTCCCCGTCACCACCCCC | 200 |
| CCCAACCCGCCCCGACCGGAGCTGAGAGTAATTCATACAA | 240 |
| AAGGACTCGCCCCTGCCTTGGGGAATCCCAGGGACCGTCG | 280 |
| TTAAACTCCCACTAACGTAGAACCCAGAGATCGCTGCGTT | 320 |
| CCCGCCCCCTCACCCGCCCGCTCTCGTCATCACTGAGGTG | 360 |
| GAGAAGAGCATGCGTGAGGCTCCGGTGCCCGTCAGTGGGC | 400 |
| AGAGCGCACATCGCCCACAGTCCCCGAGAAGTTGGGGGGA | 440 |
| GGGGTCGGCAATTGAACCGGTGCCTAGAGAAGGTGGCGCG | 480 |
| GGGTAAACTGGGAAAGTGATGTCGTGTACTGGCTCCGCCT | 520 |
| TTTTCCCGAGGGTGGGGGAGAACC<u>GTATATAA</u>GTGCAGTA | 560 |
| GTCGCCGTGAACGTTCTTTTTCGCAACGGGTTTGCCGCCA | 600 |
| GAACACAGGTAAGTGCCGTGTGTGGTTCCCGCGGGCCTGG | 640 |
| CCTCTTTACGGGTTATGGCCCTTGCGTGCCTTGAATTACT | 680 |
| TCCACGCCCCTGGCTGCAGTACGTGATTCTTGATCCCGAG | 720 |
| CTTCGGGTTGGAAGTGGGTGGGAGAGTTCGAGGCCTTGCG | 760 |
| CTTAAGGAGCCCCTTCGCCTCGTGCTTGAGTTGAGGCCTG | 800 |
| GCCTGGGCGCTGGGGCCGCCGCGTGCGAATCTGGTGGCAC | 840 |
| CTTCGCGCCTGTCTCGCTGCTTTCGATAAGTCTCTAGCCA | 880 |
| TTTAAAATTTTTGATGACCTGCTGCGACGCTTTTTTTCTG | 920 |
| GCAAGATAGTCTTGTAAATGCGGGCCAAGATCTGCACACT | 960 |
| GGTATTTCGGTTTTTGGGGCCGCGGGCGGCGACGGGGCCC | 1000 |
| GTGCGTCCCAGCGCACATGTTCGGCGAGGCGGGGCCTGCG | 1040 |
| AGCGCGGCCACCGAGAATCGGACGGGGGTAGTCTCAAGCT | 1080 |
| GGCCGGCCTGCTCTGGTGCCTGGCCTCGCGCCGCCGTGTA | 1120 |
| TCGCCCCGCCCTGGGCGGCAAGGCTGGCCCGGTCGGCACC | 1160 |
| AGTTGCGTGAGCGGAAAGATGGCCGCTTCCCGGCCCTGCT | 1200 |

(Arrows indicate positions 220, 223, and 204)

-continued

```
GCAGGGAGCTCAAAATGGAGGACGCGGCGCTCGGGAGAGC      1240

GGGCGGGTGAGTCACCCACACAAAGGAAAGGGCCTTTCC       1480

GTCCTCAGCCGTCGCTTCATGTGACTCCACGGAGTACCGG      1320

GCGCCGTCCAGGCACCTCGATTAGTTCTCGAGCTTTTGGA      1360

GTACGTCGTCTTTAGGTTGGGGGGAGGGGTTTTATGCGAT      1400

GGAGTTTCCCCACACTGAGTGGGTGGAGACTGAAGTTAGG      1440

CCAGCTTGGCACTTGATGTAATTCTCCTTGGAATTTGCCC      1480

TTTTTGAGTTTGGATCTTGGTTCATTCTCAAGCCTCAGAC      1520

AGTGGTTCAAAGTTTTTTTCTTCCATTTCAGGTGTCGTGA      1560
```

A  1561
↑
↑ 321.... (SEQ ID No:1).

Preferably, the novel DNA fragment may contain at least a portion or a whole of the base sequence of the present invention.

It is known commonly that chromosomal DNA sequences, excluding structural genes, vary from one another by slight degrees depending on the host cells, mutations and the like, without altering the main activity. Accordingly, it is intended to include within the scope of the present invention all variations of the novel DNA fragment of the present invention and the novel base sequence represented by SEQ ID No:1, wherein the base sequence is slightly modified by artificial mutation and the like, on the condition that the function of these variants is the same as that of the SV40 replication origin or the DNA of the promoter region of human EF-1α gene.

BRIEF DESCRIPTION OF THE DRAWINGS

FIG. 1—1 to 1-2 represents the base sequence of human polypeptide chain elongation factor-1α cDNA (SEQ ID NO: 6).

FIG. 2 represents the organization of human polypeptide chain elongation factor-1α chromosomal gene and diagrammatic view of the sequencing strategy including the direction and length of sequence.

FIG. 3-1 to 3-4 represents the complete base sequence of human polypeptide chain elongation factor-1α chromosomal gene (SEQ ID NO: 7).

FIG. 4 is a flow diagram for the construction of plasmids pEF-2 and pEF-3.

FIG. 10 is a result of CAT assay in IMR-32 cells.

FIGS. 11 and 12 show results of the detection of T antigen in IMR-32 cells by means of a fluorescence antibody technique, FIGS. 13 and 14 show results of the detection of T antigen in 3Y1 cells by the same technique and FIG. 15 shows a result of the detection of human CD4 in CHO-K1 cells by the same technique.

FIG. 17-1 to 17-2 is a diagram of the construction of an expression plasmid pEF-BOS.

DESCRIPTION OF THE PREFERRED EMBODIMENTS OF THE INVENTION

Figure 2:
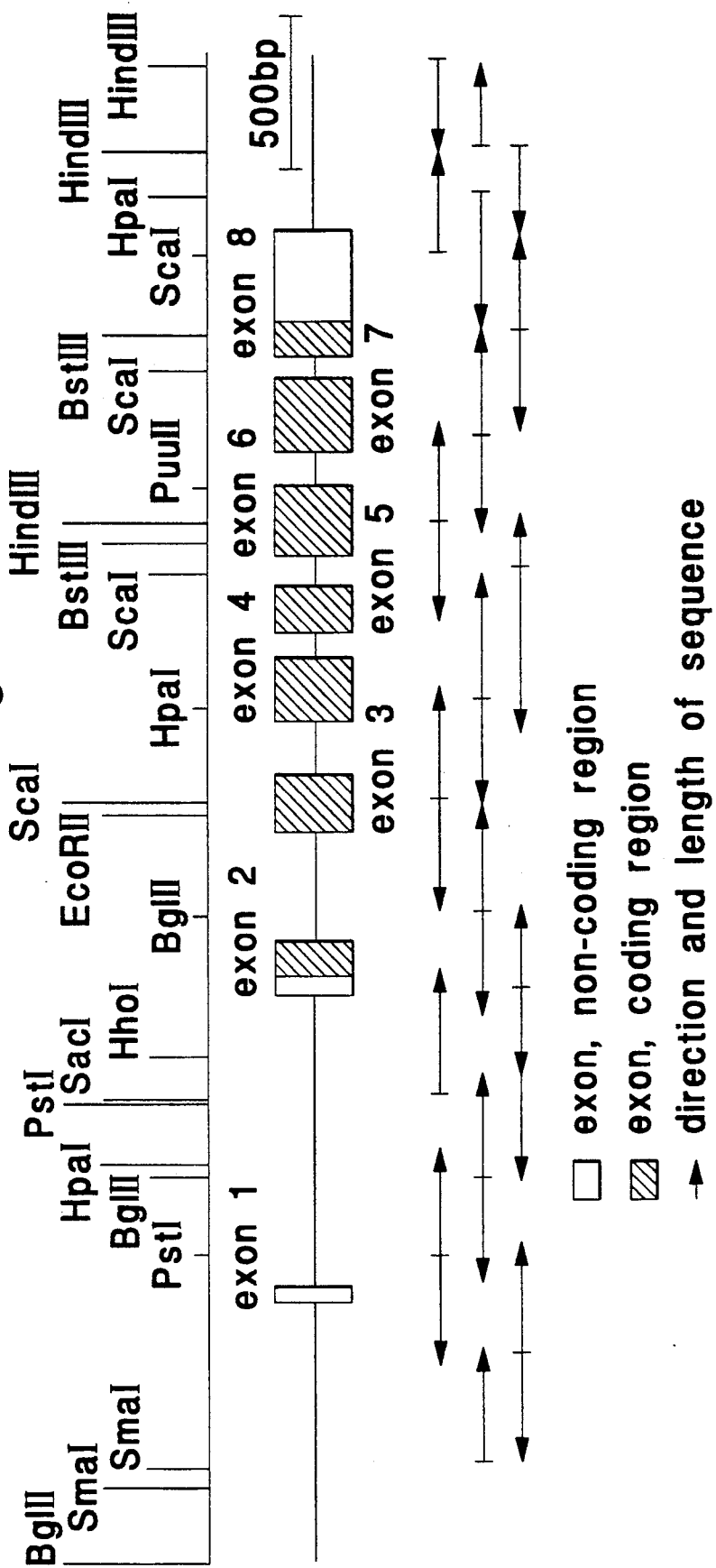

Human EF-1α chromosomal gene, including the promoter region, may be obtained by means of nucleic acid Southern blot hybridization with a human gene library using an appropriate probe. The gene library constructed from human fetal liver (R. M. Lawn et al. 1978. *Cell* 15:1157), human placenta (H. Matsushime et al. (1986) *Mol. Cell. Biol.* 6:3000) and the like can be used as the human gene library.

The human EF-1α promoter region may also be obtained in accordance with the method of T. Uetsuki et al. (*J. Biol. Chem.* 264:5791; 1989) or by chemically synthesizing it based on the report of Uetsuki et al.

Preferably, however, the DNA fragment of interest may be isolated from plasmids in which human EF-1α promoter region has already been incorporated, such as plasmid pEF-321, pEF-204, pEF-223 or pEF-220 prepared by D. W. Kim et al. (*Gene* 91:217; 1990); or co-pending U.S. application Ser. No. 07/447,823, filed Dec. 8, 1989, both of which are herein incorporated by reference. Of the cited plasmids, pEF-321 may be most convenient from the point of view of high efficiency.

Regarding a probe for use in the screening, any DNA or RNA preparation having the base sequence or complementary sequence of human EF-1α may be useful. The DNA or RNA preparation may be obtained from any eucaryotic origin, preferably from human tissues. More preferably, human EF-1α cDNA or an oligonucleotide having complementary base sequence to the cDNA may be used. Radiation labeling of human EF-1α cDNA may be performed using a commercially available nick translation kit and the like. A cDNA or an oligonucleotide having a complementary base sequence to the cDNA synthesized using a DNA synthesizer may also be used as a probe after labeling with [γ-$^{32}$P]. It is known that human chromosomes have pseudogenes, each of which have the same DNA sequence of a certain gene, but which show no function. For the purpose of avoiding cloning of the pseudogene, it is preferable to use a DNA sequence which has no homology between the cDNA and EF-1α pseudogene. A base sequence of the 3' non-coding region of the human EF-1α cDNA is suitable for this purpose.

In this case, it is necessary to confirm the presence of the coding region for the human EF-1α cDNA in the positive clones thus obtained, by means of Southern hybridization and the like using said coding region as the probe. Also, it is necessary to confirm, by determining base sequence of a positive clone, that the positive clone is identical with the EF-1α chromosomal gene, but not a pseudogene which is processed by deletion, insertion or mutation.

The human EF-1α chromosomal gene thus obtained is then subcloned into a commonly used plasmid. Any plasmid may be useful. pUC plasmids are preferable. A restriction enzyme digestion map of a plasmid thus prepared can be obtained by digesting the plasmid with various restriction enzymes. Human EF-1α chromosomal gene is digested into appropriately sized DNA fragments according to the restriction enzyme digestion map, and these DNA fragments are subcloned into phage vector M13 mp8 or M13 mp9. Single-stranded DNA fragments are isolated from the subclones and their base sequences are determined by dideoxy chain termination method. The complete nucleotide sequence of human EF-1α chromosomal gene will be determined based on the base sequence of these DNA fragments. The location of exons and introns is determined by comparing the DNA sequences of human EF-1α cDNA with that of the human EF-1α chromosomal gene.

Also, the transcription initiation site is determined by the primer extension method using an mRNA extracted from a human cell line and a synthetic oligonucleotide which is complementary to human EF-1α cDNA. A typical TATA box found in the promoter region of human EF-1α gene was located at about 30 nucleotides upstream [underlined position in SEQ ID No:1] of the transcription initiation site [marked position with * in SEQ ID No:1].

The novel DNA fragment of the present invention is in no way to be taken as limited by the condition that it contains the promoter region of above-described human polypeptide chain elongation factor gene and has an expression function of a protein in mammalian cells as the host. Also, the novel DNA fragment of the present invention may include a DNA fragment containing a promoter region of human polypeptide chain elongation factor-1α gene, a DNA fragment further comprising at least a portion of a region of about 2.5 kilo base pairs which is located immediately upstream of the initiation codon of the human polypeptide chain elongation factor-1α gene, a DNA fragment containing at least a portion of the above-described base sequence (SEQ ID No:1), and any of these DNA fragments wherein at least one base of the base sequence is modified by mutation, deletion or insertion.

These novel DNA fragments of the present invention may be obtained either by organic chemical synthesis or the method described above.

Construction of an expression plasmid using a novel DNA fragment containing a promoter region of human EF-1α gene may be performed, for example, as follows.

Cloned human EF-1α chromosomal gene is digested with EcoRI and then isolated by appropriate means such as an agarose gel electrophoresis. The isolated DNA fragment is cut with a restriction enzyme SacI which has the only one cutting site in human EF-1α gene intron 1, thus yielding two DNA fragments; one containing the promoter region, exon 1 and a part of the intron 1 and the other containing all exons excluding exon 1. Each of the two DNA fragments is isolated and subcloned into an appropriate plasmid, preferably pUC 119, which has one EcoRI recognition site and one SacI recognition site. Of the resulting two plasmids, the promoter-region-containing plasmid is cut with a restriction enzyme PstI and then treated with a nuclease Bal31. The treated fragment is then ligated with HindIII linker to make it into a circular plasmid. Some types of plasmids having different insertion sites of HindIII, that is, a plasmid containing exon 1 and its upstream part and the other plasmid which does not contain exon 1, may be obtained depending on the degree of the Bal31 reaction.

A plasmid containing the upstream part of human EF-1α gene immediately before the initiation codon ATG in exon 2 may be constructed as follows. First, one of the above-described plasmids, which contains the downstream part of the gene starting with exon 2 and including all other downstream exons, is cut with a restriction enzyme BglII and treated with a nuclease Bal31. The treated fragment is then ligated with EcoRI linker to make it into a circular plasmid. In this manner, a plasmid containing a fragment starting from the SacI cut site to the site immediately before the initiation codon is obtained. The plasmid thus obtained is digested with EcoRI, the terminal of the resulting fragment is smoothed using T4 DNA polymerase and the smooth-end is connected with HindIII linker. A human EF-1α chromosomal gene-originated SacI-HindIII fragment is isolated from the HindIII linker-connected fragment and subcloned into pUC 119. Then, the SacI-HindIII fragment subcloned into pUC 119 is reisolated by digesting the plasmid with SacI and HindIII and inserted into the SacI-HindIII site of the previously constructed plasmid which contains the promoter region of human EF-1α gene covering the upstream part of the SacI site in intron 1. In this way, a plasmid containing promoter region of human EF-1α gene covering the upstream nucleotide sequence immediately before the initiation codon in exon 2 is constructed.

There are many methods for the measurement of the expression efficiency. It is preferable to use chloramphenicol acetyltransferase (referred to as CAT hereinafter) gene and the like for the purpose of easy measuring. For example, the amount of expressed CAT gene may be measured as the formation rate of acetylated product of chloramphenicol using thin-layer chromatography and the like. When a gene other than CAT is used, the expression efficiency may be measured by a fluorescence antibody technique and the like.

Practically, construction of an expression plasmid is performed by the following procedure. DNA fragments containing a promoter region of human EF-1α gene are obtained by digesting the above-described various plasmids with SacI and HindIII. A DNA fragment encoding CAT gene is obtained by cutting it out from a CAT gene-containing plasmid and the like using appropriate restriction enzymes. For example, a CAT gene-containing DNA fragment can be cut out from pSV2-CAT plasmid using HindIII and BamHI. An expression plasmid which fits for the purpose is constructed by inserting the CAT gene-containing fragment into an appropriate plasmid previously cut with BamHI, HincII and the like, together with a DNA fragment containing promoter region of human EF-1α gene.

For example, the present inventors have constructed four expression plasmids, pEF220-CAT, pEF223-CAT, pEF204-CAT and pEF321-CAT, wherein nucleotide sequences from 5′ end to 220 ↑, to 223 ↑, to 204 ↑ and to 321 ↑ shown in the base sequence SEQ ID No:1 of the DNA fragment containing promoter region of human EF-1α chromosomal gene are inserted respectively. These four plasmids, named *E. coli* DH5 (pEF220-CAT), *E. coli* DH5 (pEF223-CAT), *E. coli* DH5 (pEF204-CAT) and *E. coli* DH5 (pEF321-CAT), have been deposited by the present inventors on Mar. 2, 1989, in Fermentation Research Institute, Agency of Industrial Science and Technology, and have been assigned the designations as FERM P-10595, FERM P-10596, FERM P-10594 and FERM P-10597, respectively.

Further, these four plasmids have been transferred to the INTERNATIONAL DEPOSITORY AUTHORITY Nov. 8, 1989, and have been assigned the designations as FERM BP-2647 (from FERM P10595), FERM BP-2648 (from FERM P-10596), FERM BP-2646 (from FERM P-10594) and FERM BP-2649 (from FERM P-10597), respectively.

Any DNA fragment may be useful as the starting material for the construction of expression plasmids of the present invention, provided that it is possessed of the same nucleotide sequence as that of the human EF-1α promoter region contained in the plasmid pEF-321. The DNA fragment containing human EF-1α promoter region comprises 2.5 kilo base pairs and contains a DNA fragment represented by the following nucleotide sequence (SEQ ID No:1):

```
CCCGGGCT GGGCT GAGACCCGC AGAGGAAGACGCT CT AGG          40
GATTTGTCCCGGACT AGCGAGAT GGCAAGGCT GAGGACGG           80
GAGGCT GATT GAGAGGCGAAGGT ACACCCT AATCTCAAT A         120
CAACCTTT GGAGCT AAGCCAGCAAT GGT AGAGGGAAGATT          160
CT GCACGTCCCTTCCAGGCGGCCT CCCCGTCACCACCCCC            200
CCCAACCCGCCCCGACCGGAGCT GAGAGT AATTCATACAA            240
AAGGACT CGCCCCT GCCTT GGGGAATCCCAGGGACCGTCG           280
TTAAACT CCCACT AACGT AGAACCCAGAGATCGCT GCGTT          320
CCCGCCCCCT CACCCGCCCGCTCTCGTCATCACT GAGGT G           360
GAGAAGAGCATGCGT GAGGCTCCGGT GCCCGTCAGT GGGC           400
AGAGCGCACATCGCCCACAGTCCCCGAGAAGTT GGGGGGA             440
GGGGTCGGCAATT GAACCGGT GCCT AGAGAAGGT GGCGCG           480
GGGT AAACT GGGAAAGT GAT GTCGT GT ACT GGCTCCGCCT         520
TTTTCCCGAGGGT GGGGGAGAACC GTATATAAGT GCAGT A           560
                                    220 ↑
GTCGCCGT GAACGTTCTTTTTCGCAACGGGTTT GCCGCCA            600
                  223 ↑              204 ↑
GAACACAGGT AAGT GCCGT GT GT GGTTCCCGCGGGCCT GG          640
CCTCTTT ACGGGTT AT GGCCCTT GCGT GCCTT GAATT ACT         680
TCCACGCCCCT GGCT GCAGT ACGT GATTCTT GATCCCGAG          720
CTTCGGGTT GGAAGT GGGT GGGAGAGTTCGAGGCCTT GCG           760
CTT AAGGAGCCCCTTCGCCTCGT GCTT GAGTT GAGGCCT G          800
GCCT GGGCGCT GGGGCCGCCGCGT GCGAATCT GGT GGCAC           840
CTTCGCGCCT GTCTCGCT GCTTTCGAT AAGTCTCT AGCCA           880
TTT AAAATTTTT GAT GACCT GCT GCGACGCT TTTTTTCT G         920
GCAAGAT AGTCTT GT AAAT GCGGGCCAAGATCT GCACACT          960
GGT ATTTCGGTTTTT GGGGCCGCGGGCGGCGACGGGGCCC           1000
GT GCGTCCCAGCGCACATGTTCGGCGAGGCGGGGCCT GCG           1040
AGCGCGGCCACCGAGAATCGGACGGGGGT AGTCTCAAGCT            1080
GGCCGGCCT GCTCT GGT GCCT GGCCTCGCGCCGCCGT GT A         1120
TCGCCCCGCCCT GGGCGGCAAGGCT GGCCCGGTCGGCACC            1160
```

-continued

```
AGTTGCGTGAGCGGAAAGATGGCCGCTTCCCGGCCCTGCT      1200
GCAGGGAGCTCAAAATGGAGGACGCGGCGCTCGGGAGAGC      1240
GGGCGGGTGAGTCACCCACACAAAGGAAAAGGGCCTTTCC      1480
GTCCTCAGCCGTCGCTTCATGTGACTCCACGGAGTACCGG      1320
GCGCCGTCCAGGCACCTCGATTAGTTCTCGAGCTTTTGGA      1360
GTACGTCGTCTTTAGGTTGGGGGGAGGGGTTTTATGCGAT      1400
GGAGTTTCCCCACACTGAGTGGGTGGAGACTGAAGTTAGG      1440
CCAGCTTGGCACTTGATGTAATTCTCCTTGGAATTTGCCC      1480
TTTTTGAGTTTGGATCTTGGTTCATTCTCAAGCCTCAGAC      1520
AGTGGTTCAAAGTTTTTTTCTTCCATTTCAGGTGTCGTGA      1560
A  1561
↑
|321.... (SEQ ID No:1).
```

When plasmid pEF-321-CAT is used as the starting material, expression plasmids which show a high expression efficiency in transient expression systems can be obtained by inserting a DNA fragment containing a SV40 replication origin into an appropriate site in each of the expression plasmids.

The SV40 replication origin can be obtained by digesting any plasmids containing the replication origin with appropriate restriction enzymes. For example, an SV40 DNA fragment (311 bp) containing a SV40 replication origin can be obtained by digesting plasmid pMLSV.

According to some of the expression plasmids of the present invention, a portion of the upstream side of the DNA fragment containing human EF-1α promoter region may be removed and replaced by a DNA fragment containing SV40 replication origin, provided that function of the human EF-1α promoter is not altered by the removal of the upstream portion. For example, an upstream portion of the DNA fragment containing human EF-1α promoter region, namely a SphI-SphI DNA fragment of about 1.3 kilo base pairs, can be replaced by a DNA fragment containing the SV40 replication origin. In the resultant expression plasmid, the fragment containing the human EF-1α promoter region comprises a nucleotide sequence represented by the following sequence (SEQ ID No:4):

```
373     CGTGAGGCTCCGGTGCCCGTCAGTGGGC         400
        AGAGCGCACATCGCCCACAGTCCCCGAGAAGTTGGGGGGA   440
        GGGGTCGGCAATTGAACCGGTGCCTAGAGAAGGTGGCGCG   480
        GGGTAAACTGGGAAAGTGATGTCGTGTACTGGCTCCGCCT   520
        TTTTCCCGAGGGTGGGGGAGAACCGTATATAAGTGCAGTA   560
        GTCGCCGTGAACGTTCTTTTTCGCAACGGGTTTGCCGCCA   600
        GAACACAGGTAAGTGCCGTGTGTGGTTCCCGCGGGCCTGG   640
        CCTCTTTACGGGTTATGGCCCTTGCGTGCCTTGAATTACT   680
        TCCACGCCCCTGGCTGCAGTACGTGATTCTTGATCCCGAG   720
        CTTCGGGTTGGAAGTGGGTGGGAGAGTTCGAGGCCTTGCG   760
        CTTAAGGAGCCCCTTCGCCTCGTGCTTGAGTTGAGGCCTG   800
        GCCTGGGCGCTGGGGCCGCCGCGTGCGAATCTGGTGGCAC   840
        CTTCGCGCCTGTCTCGCTGCTTTCGATAAGTCTCTAGCCA   880
        TTTAAAATTTTTGATGACCTGCTGCGACGCTTTTTTTCTG   920
        GCAAGATAGTCTTGTAAATGCGGGCCAAGATCTGCACACT   960
        GGTATTTCGGTTTTTGGGGCCGCGGGCGGCGACGGGGCCC   1000
        GTGCGTCCCAGCGCACATGTTCGGCGAGGCGGGGCCTGCG   1040
        AGCGCGGCCACCGAGAATCGGACGGGGGTAGTCTCAAGCT   1080
        GGCCGGCCTGCTCTGGTGCCTGGCCTCGCGCCGCCGTGTA   1120
        TCGCCCCGCCCTGGGCGGCAAGGCTGGCCCGGTCGGCACC   1160
```

```
AGTTGCGTGAGCGGAAAGATGGCCGCTTCCCGGCCCTGCT      1200

GCAGGGAGCTCAAAATGGAGGACGCGGCGCTCGGGAGAGC      1240

GGGCGGGTGAGTCACCCACACAAAGGAAAAGGGCCTTTCC      1480

GTCCTCAGCCGTCGCTTCATGTGACTCCACGGAGTACCGG      1320

GCGCCGTCCAGGCACCTCGATTAGTTCTCGAGCTTTTGGA      1360

GTACGTCGTCTTTAGGTTGGGGGGAGGGGTTTTATGCGAT      1400

GGAGTTTCCCCACACTGAGTGGGTGGAGACTGAAGTTAGG      1440

CCAGCTTGGCACTTGATGTAATTCTCCTTGGAATTTGCCC      1480

TTTTTGAGTTTGGATCTTGGTTCATTCTCAAGCCTCAGAC      1520

AGTGGTTCAAAGTTTTTTTCTTCCATTTCAGGTGTCGTGA      1560

A      1561                                  (SEQ ID No:4).
```

For the purpose of exhibiting the function of the expression plasmid of the present invention in mammalian cells, it is necessary to add a polyadenylation signal to the plasmid. The SV40 polyadenylation signal contained in plasmid pEF-321-CAT may be conveniently used for this purpose, as well as those in other genes such as the polyadenylation signal in human granulocyte-colony stimulating factor (G-CSF).

In addition, the expression plasmid of the present invention may preferably have appropriate restriction enzyme recognition sites downstream of its promoter region, so that a gene to be expressed or cloned can be inserted easily into a region downstream of the promoter region. For this purpose, various cloning site-containing DNA fragments can be used, such as a stuffer fragment of plasmid CDM8. This stuffer fragment has an advantage in that self-ligation does not occur when BstXI recognition sites contained in the fragment are used in cloning. The stuffer fragment can be isolated from plasmid CDM8 as a XbaI-XbaI DNA fragment (451 bp).

When the expression plasmid contains a recognition site identical to its cloning site, the object of the present invention can be attained by removing the recognition site. Even when such a recognition site is found in a DNA fragment containing human EF-1α promoter region, a DNA fragment containing a SV40 replication origin or a DNA fragment containing a polyadenylation signal, the recognition site can be removed without inconvenience so long as the basic functions of these DNA fragments are not changed by the removal. For example, removal of BstXI recognition site from a DNA fragment containing human EF-1α promoter region does not alter the function of the promoter region. In this instance, the fragment containing human EF-1α promoter region comprises a nucleotide sequence represented by the following sequence (SEQ ID No:5):

```
373      CGTGAGGCTCCGGTGCCCGTCAGTGGGC       400

AGAGCGCACATCGCCCACAGTCCCCGAGAAGTTGGGGGGA    440

GGGGTCGGCAATTGAACCGGTGCCTAGAGAAGGTGGCGCG    480

GGGTAAACTGGGAAAGTGATGTCGTGTACTGGCTCCGCCT    520

TTTTCCCGAGGGTGGGGGAGAACCGTATATAAGTGCAGTA    560

GTCGCCGTGAACGTTCTTTTTCGCAACGGGTTTGCCGCCA    600

GAACACAGGTAAGTGCCGTGTGTGGTTCCCGCGGGCCTGG    640

CCTCTTTACGGGTTATGGCCCTTGCGTGCCTTGAATTACT    680

TCCAC    CTGGCTGCAGTACGTGATTCTTGATCCCGAG    720

CTTCGGGTTGGAAGTGGGTGGGAGAGTTCGAGGCCTTGCG    760

CTTAAGGAGCCCCTTCGCCTCGTGCTTGAGTTGAGGCCTG    800

GCCTGGGCGCTGGGGCCGCCGCGTGCGAATCTGGTGGCAC    840

CTTCGCGCCTGTCTCGCTGCTTTCGATAAGTCTCTAGCCA    880

TTTAAAATTTTTGATGACCTGCTGCGACGCTTTTTTTCTG    920

GCAAGATAGTCTTGTAAATGCGGGCCAAGATCTGCACACT    960

GGTATTTCGGTTTTTGGGGCCGCGGGCGGCGACGGGGCCC    1000

GTGCGTCCCAGCGCACATGTTCGGCGAGGCGGGGCCTGCG    1040

AGCGCGGCCACCGAGAATCGGACGGGGGTAGTCTCAAGCT    1080
```

```
GGCCGGCCTGCTCTGGTGCCTGGCCTCGCGCCGCCGTGTA         1120

TCGCCCCGCCCTGGGCGGCAAGGCTGGCCCGGTCGGCACC         1160

AGTTGCGTGAGCGGAAAGATGGCCGCTTCCCGGCCCTGCT         1200

GCAGGGAGCTCAAAATGGAGGACGCGGCGCTCGGGAGAGC         1240

GGGCGGGTGAGTCACCCACACAAAGGAAAAGGGCCTTTCC         1480

GTCCTCAGCCGTCGCTTCATGTGACTCCACGGAGTACCGG         1320

GCGCCGTCCAGGCACCTCGATTAGTTCTCGAGCTTTTGGA         1360

GTACGTCGTCTTTAGGTTGGGGGAGGGGTTTTATGCGAT          1400

GGAGTTTCCCCACACTGAGTGGGTGGAGACTGAAGTTAGG         1440

CCAGCTTGGCACTTGATGTAATTCTCCTTGGAATTTGCCC         1480

TTTTTGAGTTTGGATCTTGGTTCATTCTCAAGCCTCAGAC         1520

AGTGGTTCAAAGTTTTTTTCTTCCATTTCAGGTGTCGTGA         1560

A     1561                                     (SEQ ID No:5).
```

A transformant was obtained by transforming an *E. coli* strain with one of the plasmids obtained by the present invention. The transformant plasmid pEF-BOS, named *E. coli* DH5 (pEF-BOS), has been deposited by one of the present inventors on Sep. 6, 1991, in Fermentation Research Institute, Agency of Industrial Science and Technology, and has been assigned the designation as FERM EP-3549.

Usefulness of the expression plasmid of the present invention can be confirmed by inserting an appropriate gene into the downstream region of the human EF-1α promoter region making use of appropriate restriction enzyme recognition sites or the like, and by subsequently checking expression efficiency of the inserted gene. As a gene to be expressed for this purpose, the CAT gene is used advantageously because its expressed amount can be judged easily, although human G-CSF cDNA is also useful. When the CAT gene is used, the amount of CAT expressed can be measured as a formation ratio of acetylated chloramphenicol using thin layer chromatography. In the case of G-CSF, the amount of product expressed can be measured by a biological assay technique using an appropriate cell line.

In addition, production of a desired physiologically active substance may be achieved using any of these expression plasmids of the present invention by substituting a gene encoding a physiologically active substance for the CAT gene in the expression plasmids. Substitution of a gene may be performed by applying necessary treatments commonly used in this field of studies. For example, it is preferable to remove the plasmid-originated HindIII recognition site in advance. Also, it is preferable to keep intact the poly-(A) signaling region in order to ensure poly-(A) addition to messenger RNA within cells.

EXAMPLES

Examples of the present invention are given below by way of illustration, and not by way of limitation.

Cell culture media used in the following examples are shown below. Each medium was prepared according to the preparation protocol attached to the medium article and used after adding kanamycin to the final concentration of 60 mg/l, except for Eagle's MEM medium.

| | |
|---|---|
| DM-160AU medium | (Kyokuto Pharmaceutical Ind. Co., Ltd.) |
| Eagle's MEM medium (MEM) | (Nissui Pharmaceutical Co., Ltd.) |
| Dulbecco's Modified Eagle's medium (DMEM) | (Nissui Pharmaceutical Co., Ltd.) |
| Ham's F12 medium (Ham's F12) | (Nissui Pharmaceutical Co., Ltd.) |
| RPMI 1640 medium | (Nissui Pharmaceutical Co., Ltd.) |

Unless otherwise stated, commonly used abbreviations in this field of study are used in the following descriptions. Each experiment in the following examples is based on the common gene manipulation techniques which can be performed in accordance with any commonly used manual, such as *Molecular Cloning, A Laboratory Manual* (Maniatis et al., Cold Spring Harbor Laboratory, 1982) and *Labomanual Gene Technology* (written in Japanese; M. Muramatsu, Maruzen Co., Ltd., 1988).

EXAMPLE I

Isolation and Identification of Human EF-1α Chromosomal Gene (1) Isolation of Human EF-1α cDNA Plasmid pNK1 containing yeast EF-1α chromosomal gene which had been constructed by K. Nagashima et al., (Gene 45:265; 1986) was digested with ClaI and HindIII, and the ClaI-HindIII fragment (ca. 1 kilo base pairs) was isolated by agarose gel electrophoresis. A probe was prepared by labeling the fragment thus isolated with [$^{32}$P] by nick translation using [α-$^{32}$P]dCTP.

A cDNA library of human fibroblast GM637 constructed by H. Okayama and P. Berg (*Mol. Cell. Biol.* 3:280; 1983) was kindly provided by Dr. Okayama at National Institute of Health. About 40,000 colonies obtained from the library were screened by colony hybridization using the above-described probe, in accordance with the conditions reported by S. Nagata et al., (*Proc. Natl. Acad. Sci.* USA 80:6192; 1983).

Figures 1, 17:
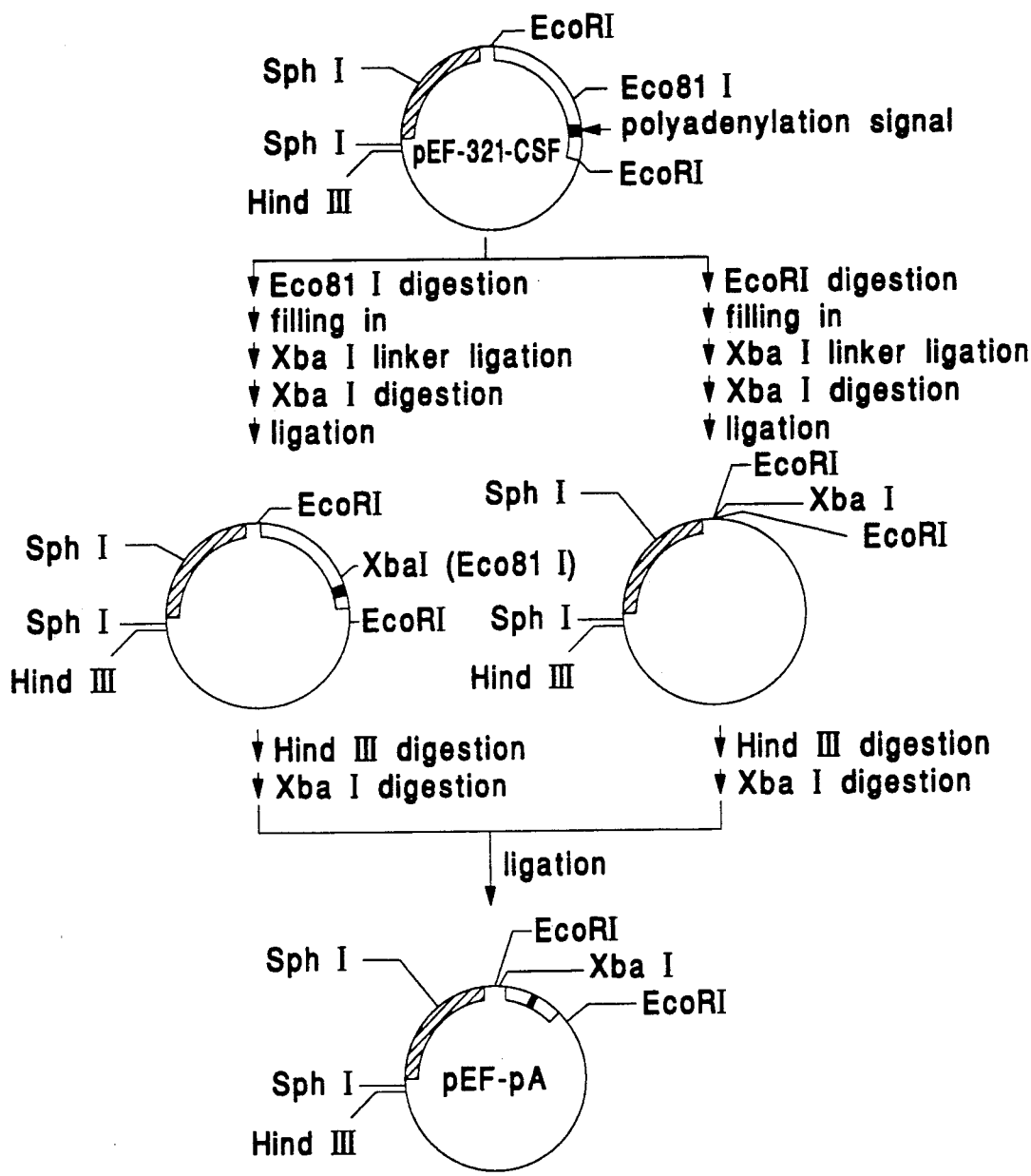
Figures 2, 17:
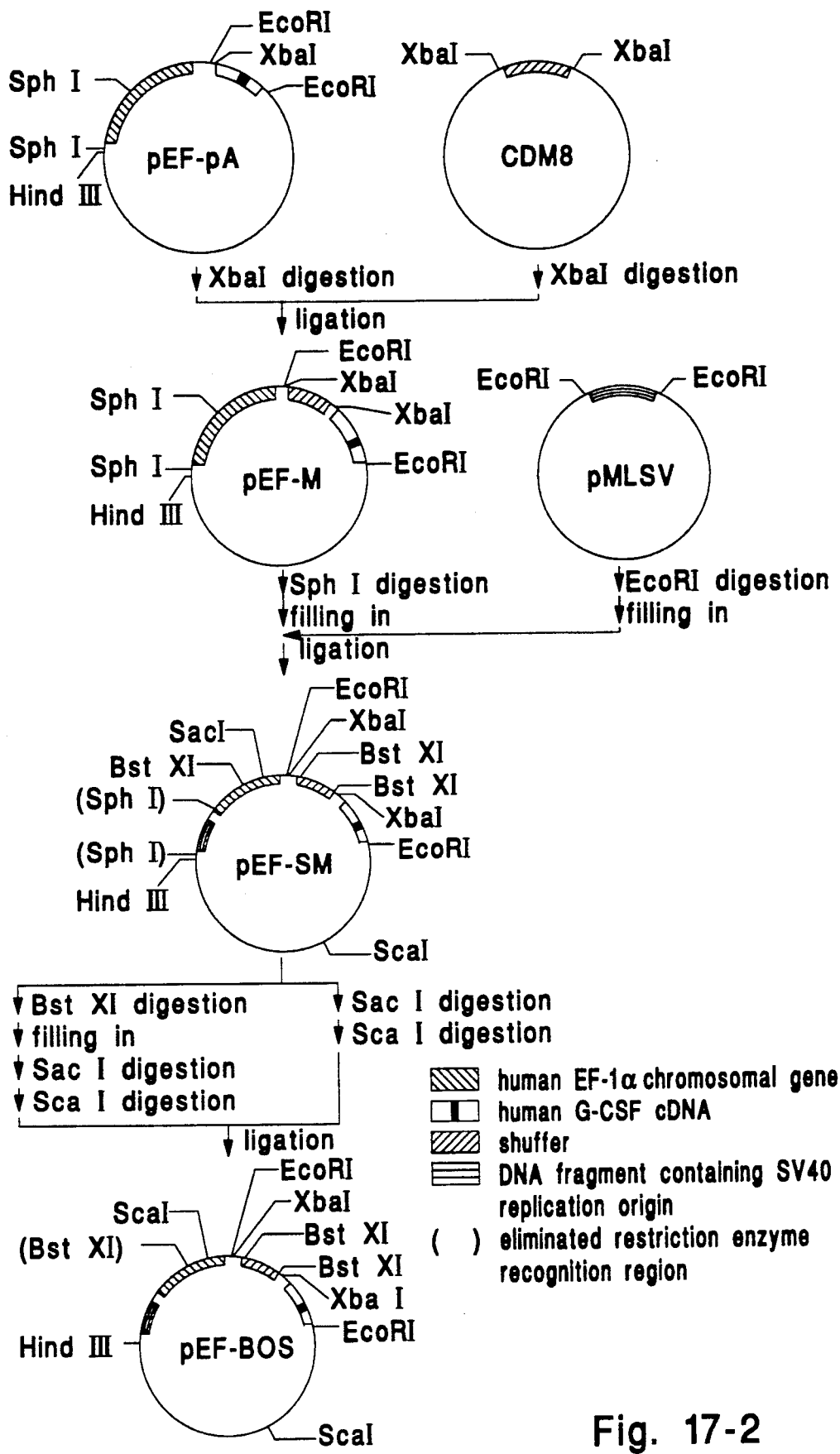

Colonies replicated on a nitrocellulose filter were hybridized at 28° C. with the probe which has been heated at 95° C. for 5 min and immediately cooled. After washing, the filter was applied to an autoradiography in order to screen clones. The length of the human EF-1α cDNA in positive clones thus obtained was analyzed by agarose gel electrophoresis, and a plasmid containing the longest cDNA (ca. 1.8 kilo base pairs) was designated pAN7. The complete base sequence of the human EF-1α cDNA was then determined by dideoxy chain termination method. The complete base sequence of human EF-1α cDNA thus obtained is shown in FIG. 1.

The result showed that the coding region for the human EF-1α cDNA gene consisted of 1386 base pairs and its base sequence was identical with the base sequence of the coding region for a human EF-1α cDNA which has been reported by J. H. G. M. Brands et al., (*Eur. J. Biochem.* 155:167; 1986).

(2) Cloning of Human EF-1α Chromosomal Gene

For the purpose of isolating human EF-1α chromosomal gene, human gene libraries were screened using the human EF-1α cDNA obtained in Example 1-(1) as the probe. Human gene libraries constructed with human fetal liver DNA (R. M. Lawn et al,; *Cell,* 15:1157; 1978) and human placenta DNA (H. Matsushime et al,; *Mol. Cell. Biol.* 6:3000; 1986) were provided by Dr. T. Maniatis at Harvard University and Dr. M. Shibuya at Institute of Medical Science, University of Tokyo, respectively. A probe was prepared by isolating a BamHI fragment (ca. 2 kilo base pairs) of human EF-1α cDNA from the above-described plasmid pAN7 and labeling the fragment with [$^{32}$P] by nick translation under the same conditions as described in Example 1-(1).

A total of about 1,500,000 plaques obtained from both human gene libraries were screened by plaque hybridization, and 218 positive clones were obtained. Five of the positive clone-containing plaques were selected at random, and their λ DNAs carrying chromosomal DNA fragments were prepared. Although chromosomal DNA fragments from these five clones hybridized strongly with human EF-1α cDNA probe, the restriction enzyme digestion mapping and the nucleotide sequencing analysis showed that they did not contain any intron but several mutations, deletions or insertions. On the basis of these results, these chromosomal DNA fragments were considered to be pseudogenes of human EF-1α.

For the purpose of isolating and identifying active human EF-1α chromosomal gene, a nucleotide sequence, (SEQ ID NO:2) consisting of 18 bases (5'-GATAACAATGCATCGTAA-3') in the 3' non-coding region of the human EF-1α cDNA (a sequence located at about 120 bases downstream of the termination codon) was synthesized using a DNA synthesizer (Applied Biosystems, Model 380A). The oligonucleotide thus synthesized was labeled with [$^{32}$P] using T4-polynucleotide kinase and [γ-$^{32}$P) and used as the probe. Using this probe, 70 of the above-described positive clones were screened again by means of plaque hybridization. As the result, 5 of the tested clones were found positive. It was confirmed that one of the 5 positive clones, named λEFg 58, contained about 7 kilo base pairs of EcoRI fragment, and this fragment contained human EF-1α chromosomal gene, because the fragment hybridized with the human EF-1α cDNA probe.

(3) Sequencing of Human EF-1α Chromosomal Gene

The human EF-1α chromosomal DNA fragment cloned into λEFg 58 obtained in Example 1-(2) was cut out with EcoRI and isolated by agarose gel electrophoresis. The 7 kilo base pair EcoRI fragment was subcloned at the EcoRI site of pUC 119 and the resulting plasmid was designated pEFg 1.

Next, the plasmid pEFg 1 was treated with various restriction enzymes and the restriction enzyme cut sites were determined based on the the number and moving rate of the bands of the digests by agarose gel electrophoresis in order to construct a restriction enzyme digestion map of human EF-1α chromosomal gene. For the purpose of determining the base sequence of the human EF-1α chromosomal gene, plasmid pEFg 1 was cut with various restriction enzymes and the DNA fragments were subcloned into M13 mp8 or M13 mp9. The single-stranded DNA was isolated according to a commonly used method and the base sequence was determined by the dideoxy chain termination method. As a result, it was confirmed that the DNA fragment cloned into the plasmid pEFg 1 was the human EF-1α chromosomal gene, because base sequence of the DNA fragment was completely identical with that of the human EF-1α cDNA. A restriction enzyme digestion map of human EF-1α chromosomal gene and the direction of the sequencing are shown in FIG. 2, and a base sequence of about 4.7 kilo bases starting at SmaI site is shown in FIG. 3.

(4) Structure of human EF-1α chromosomal gene

The human EF-1α cDNA obtained in Example 1-(1) and the human EF-1α chromosomal gene obtained in Example 1-(3) were compared in order to determine the position of exons and introns. As a result, it was found that the chromosomal gene comprised 8 exons and 7 introns (FIG. 2).

The transcription initiation site of human EF-1α gene was determined by the primer extension method. A single-stranded cDNA fragment was synthesized using 5 μg of mRNA obtained from human HL-60 cells, 5 pmol of [$^{32}$P]-labeled oligonucleotide (SEQ ID NO:3) (5'-TGTGTTCTGGCGGCAAACCCGTTG-3') which is complementary to the nucleotide positions 584 to 607 shown in FIG. 3, 25 units of AMV reverse transcriptase and 40 units of RNase inhibitor. The transcription initiation site (the position marked with * in FIG. 3) was determined by analyzing the single-stranded cDNA fragment thus obtained by means of 7M urea-containing 8% polyacrylamide gel electrophoresis.

On the basis of these results, it was found that exon 1 consisted of 33 bases, the initiation codon ATG was located in exon 2, and the sequence of intron 1 between the exons 1 and 2 consisted of 943 bases.

EXAMPLE 2

Construction of CAT Gene Expression Plasmid Containing Promoter Region of Human EF-1α Gene (1) Construction of Plasmids pEF-2 and pEF-3

Figure 4:
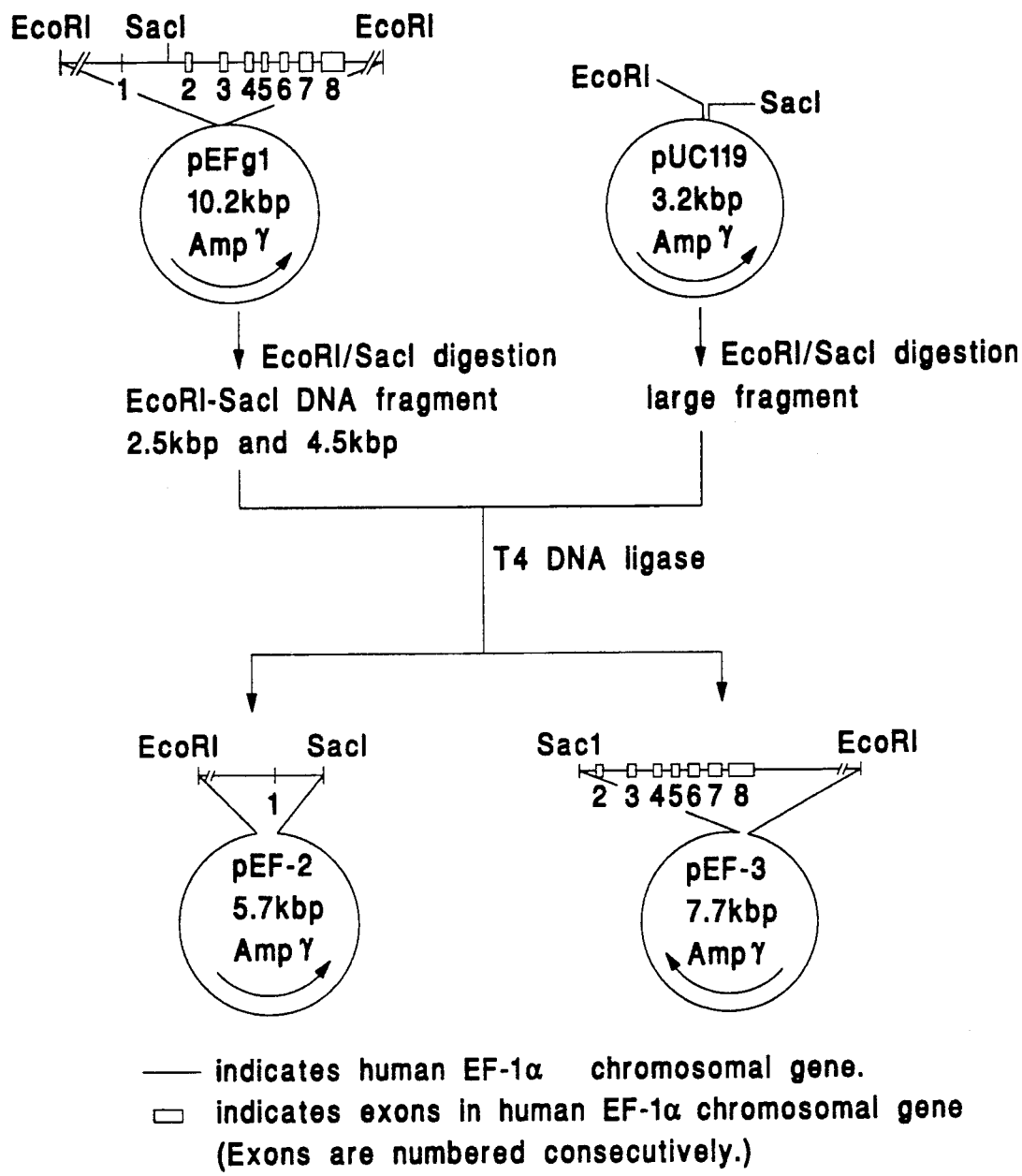

A flow diagram for the construction of these plasmids is shown in FIG. 4. The human EF-1α gene-containing EcoRI fragment (ca. 7 kilo base pairs) in plasmid pEFg 1 was digested with SacI and EcoRI, and two DNA fragments (about 2.5 and 4.5 kilo base pairs, respectively) were isolated by agarose gel electrophoresis. Each of the two DNA fragments was subcloned at the site between EcoRI and SacI of plasmid PUC 119. One plasmid containing a promoter region of human EF-1α gene and exon 1 was designated pEF-2 and the other plasmid containing exons 2 to 8 was designated pEF-3.

(2) Construction of Plasmids pEF-220, pEF-223 and pEF-204

Figure 5:
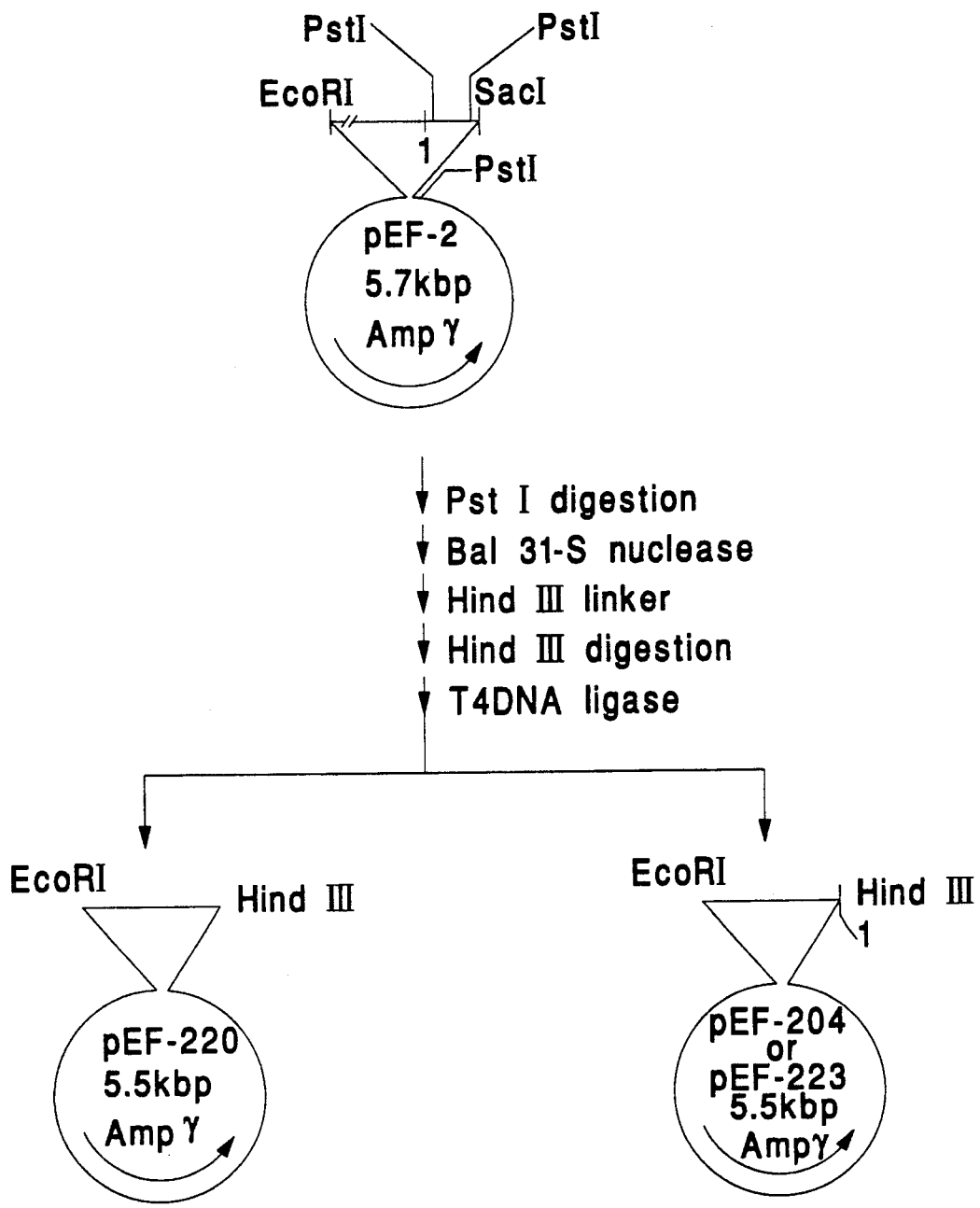
FIG. 5 is a flow diagram for the construction of plasmids pEF-220, pEF-223 and pEF-204.

A flow diagram for the construction of these plasmids is shown in FIG. 5. A 10 μg portion of plasmid pEF-2 prepared in Example 2-(1) was digested with PstI and incubated at 30° C. for 10 min in the presence of 3 units of Bal31-S nuclease (Takara Shuzo Co. Ltd.). To the Bal31-S digested DNA fragments 1 μg of 5'-phosphorylated HindIII linker pCAAGCTTG (Takara Shuzo Co., Ltd.) was ligated using T4 DNA ligase. Plasmids containing HindIII recognition site were obtained by digesting the linker-added fragment with HindIII and making the digests into circular plasmids using T4 DNA ligase. Although the inserted position of HindIII recognition region into these plasmids varied, the region of human EF-1α chromosomal DNA in each plasmid was revealed precisely by determining the base sequence of each plasmid by the dideoxy chain termination method using the plasmid DNA as the template (upstream-directed sequencing started from HindIII site). Of these, the following 3 plasmids were selected for use in the construction of the expression plasmid; that is, a plasmid designated pEF-220 containing an upstream region of human EF-1α chromosomal gene between the EcoRI site and a site [220 ↑ in SEQ ID No:1] 21 bases upstream of the transcription initiation site; a plasmid designated pEF-223 containing an upstream region of the gene between the EcoRI site and a site [223 ↑ in SEQ ID No:1] 8 bases downstream of the transcription initiation site;and a plasmid designated pEF-204 containing an upstream region of the gene between the EcoRI site and a site [204 ↑ in SEQ ID No:1] 24 bases downstream of the transcription initiation site.

(3) Construction of Plasmid pEF-321

Figure 6:
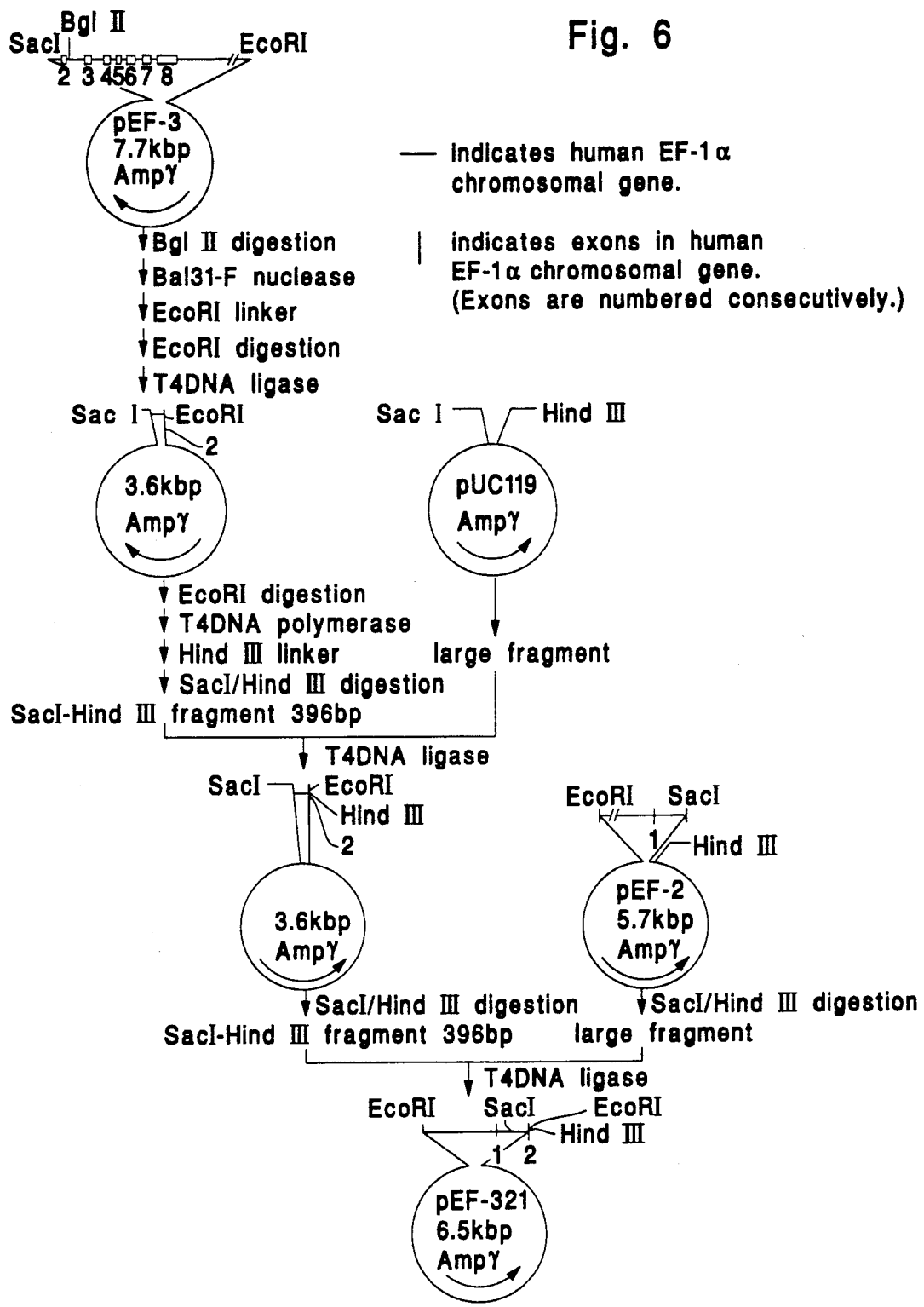
FIG. 6 is a flow diagram for the construction of plasmid pEF-321.

A flow diagram for the construction of this plasmid is shown in FIG. 6. A 5 μg portion of plasmid pEF-3 prepared in Example 2-(1) was digested with BglII and incubated at 30° C. for 8 min in the presence of 1.3 unit of Bal31-F nuclease (Takara Shuzo Co., Ltd.). To the Bal31-F digested DNA fragment 1 μg of 5'-phosphorylated EcoRI linker pGGAATTCC (Takara Shuzo Co., Ltd.) was ligated using T4 DNA ligase. Plasmids containing a region between SacI site and a site in exon 2 were obtained by digesting the linker-added fragment with EcoRI and making the digests into circular plasmids using T4 DNA ligase. The inserted position of EcoRI recognition region was determined by the same sequencing technique as described in Example 2-(2), and a plasmid containing a region between the SacI site and a site 10 bases downstream of the 5'end of exon 2 [a site marked with 32 ↑ in SEQ ID No:1] was selected.

The plasmid thus obtained was cut with EcoRI, and the resulted fragment was smooth-ended using T4 DNA polymerase and ligated with HindIII linker in the same manner as described in Example 2-(2). A SacI-HindIII fragment (396 base pairs) containing a portion of exon 2 (10 base length) was isolated from the linker-added DNA fragment and inserted between the SacI site and HindIII site of pUC 119 using T4 DNA ligase. Plasmid pEF-321 was obtained by reisolating the SacI-HindIII fragment from the resulted plasmid and inserting the fragment between the SacI site and HindIII site of plasmid pEF-2 prepared in Example 2-(1) using T4 DNA ligase. The plasmid pEF-321 contains a region of human EF-1α chromosomal gene ranging from the upstream EcoRI site of the gene to the first 10 bases in the exon 2 (a site 21 base-upstream of the initiation codon ATG).

Figure 7:
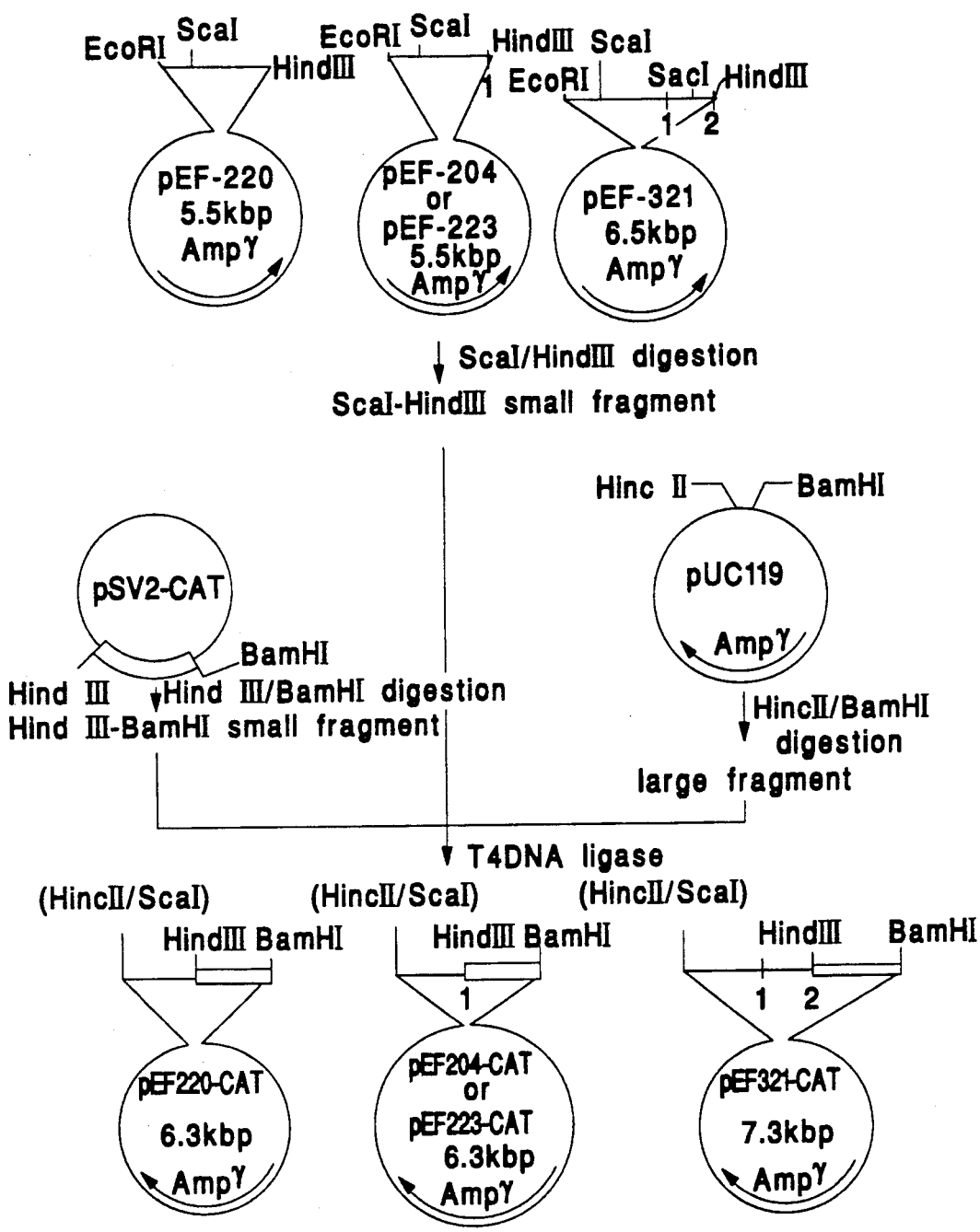
FIG. 7 is a flow diagram for the construction of plasmids pEF220-CAT, pEF223-CAT, pEF204-CAT and pEF321-CAT.

(4) Construction of Plasmids pEF204-CAT, pEF223-CAT, pEF220-CAT and pEF321-CAT A flow diagram for the construction of these plasmids is shown in FIG. 7. Plasmid pEF-220, pEF-223 or pEF-204 obtained in Example 2-(2) or plasmid pEF-321 obtained in Example 2-(3) was digested with SacI and HindIII and a SacI-HindIII fragment containing a promoter region of human EF-1α gene was isolated. CAT gene was isolated as a DNA fragment consisting of about 1.6 kilo base pairs from plasmid pSV2-CAT (C. M. Gorman et al. (1982) *Mol. Cell. Biol.* 2:1044) kindly provided by Dr. P. Berg at Stanford University, by digesting the plasmid with HindIII and BamHI.

These two DNA fragments and a HincII-BamHI large fragment (3.2 kilo base pairs) obtained from plasmid pUC 119 were connected using T4 DNA ligase. Plasmids pEF220-CAT, pEF223-CAT, pEF204-CAT and pEF321-CAT were prepared in this way. Each SacI-HindIII fragment of these plasmids contains additional sequence of about 950 base pairs attached to the 5'-end of the base sequence, SEQ ID No:1.

EXAMPLE 3

Figure 8:
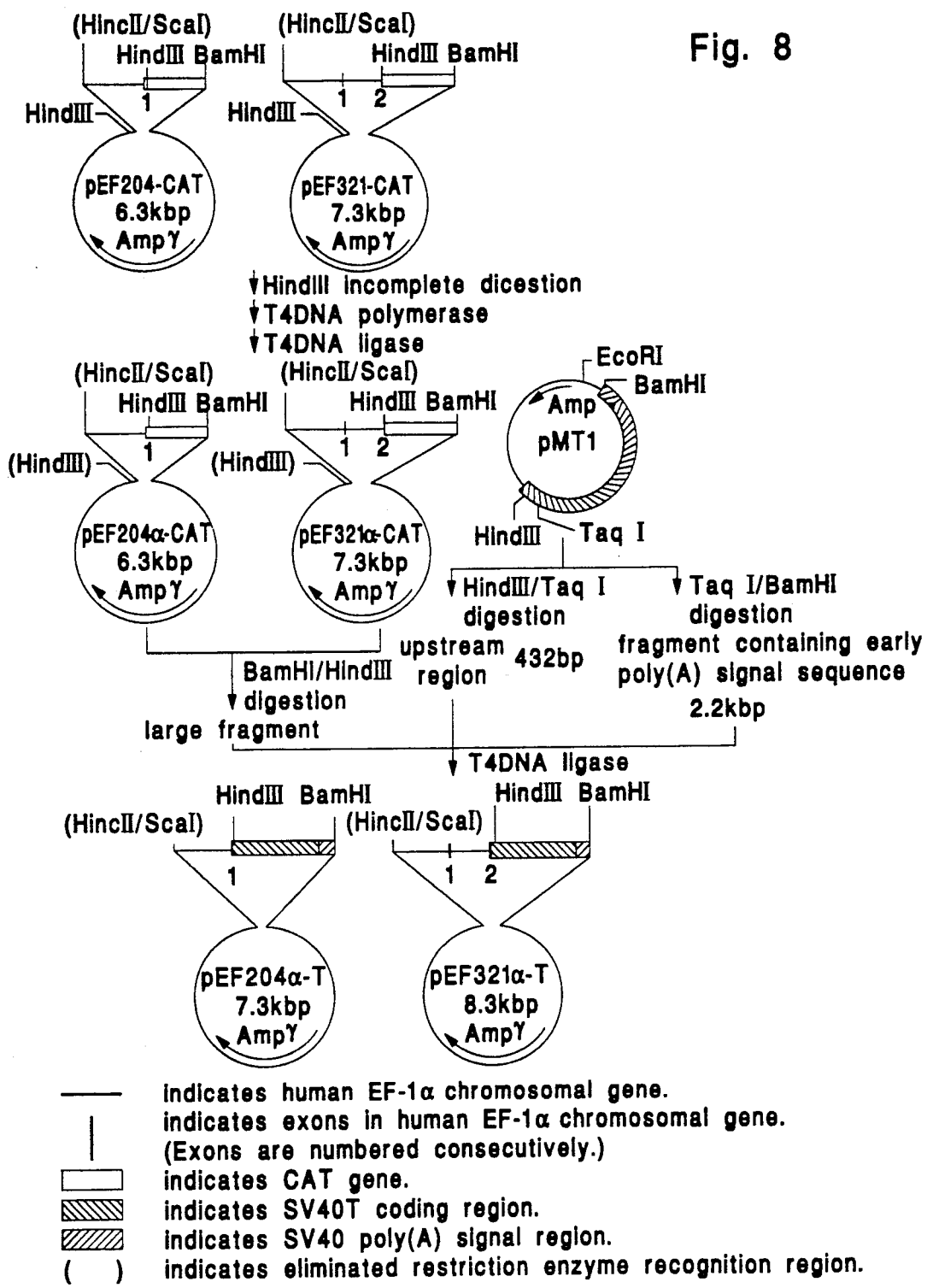
FIG. 8 is a flow diagram for the construction of plasmids pEF204α-T and pEF321α-T.

Construction of SV40 T Antigen Expression Plasmids Containing Promoter Region of Human EF-1α Gene A flow diagram for the construction of these plasmids is shown in FIG. 8.

(1) Construction of Plasmids pEF204α-CAT and pEF321α-CAT

For the purpose of removing the pUC 119-originated HindIII recognition site selectively, incomplete digestion of plasmids pEF204-CAT and pEF321-CAT was performed by incubating 4 μg of each plasmid at 37° C. for 10, 15, 25 or 40 min in the presence of 6 units of HindIII. DNA fragments produced by digestion of the plasmid at only one cut site were isolated and purified by agarose gel electrophoresis. The purified DNA fragments were smooth-ended using T4 DNA polymerase and then ligated with T4 DNA ligase. These plasmids thus obtained were digested with HindIII and BamHI and a plasmid from which the CAT gene-originated DNA fragment (1.6 kilo base pairs) was able to be cut out by the digestion was selected. In this way, plasmids named pEF204α-CAT and pEF321α-CAT were obtained from pEF204-CAT and pEF321-CAT, respectively.

(2) Construction of Plasmids pEF204α-T and pEF321α-T

Plasmid pMT1 containing the coding region of SV40 T antigen (S. Sugano et al. *J. Virol.* 52:884; 1984) was digested with HindIII and TaqI and an upstream fragment (432 base pairs) of the coding region of SV40 T antigen was isolated. Separately from this experiment, plasmid pMT1 was digested with TaqI and BamHI and a downstream fragment (2.2 kilo base pairs), containing early poly (A) signaling sequence, of the coding region of SV40 T antigen was isolated.

The CAT gene in each of the plasmids pEF204α-CAT and pEF321α-CAT prepared in Example 3-(1) was removed by digesting each plasmid with HindIII and BamHI. The region between HindIII site and BamHI site thus emptied was inserted with both HindIII-TaqI and TaqI-BamHI fragments described above. In this manner, plasmids pEF204α-T and pEF321α-T containing entire coding region of SV40 T antigen were constructed.

EXAMPLE 4

Figure 9:
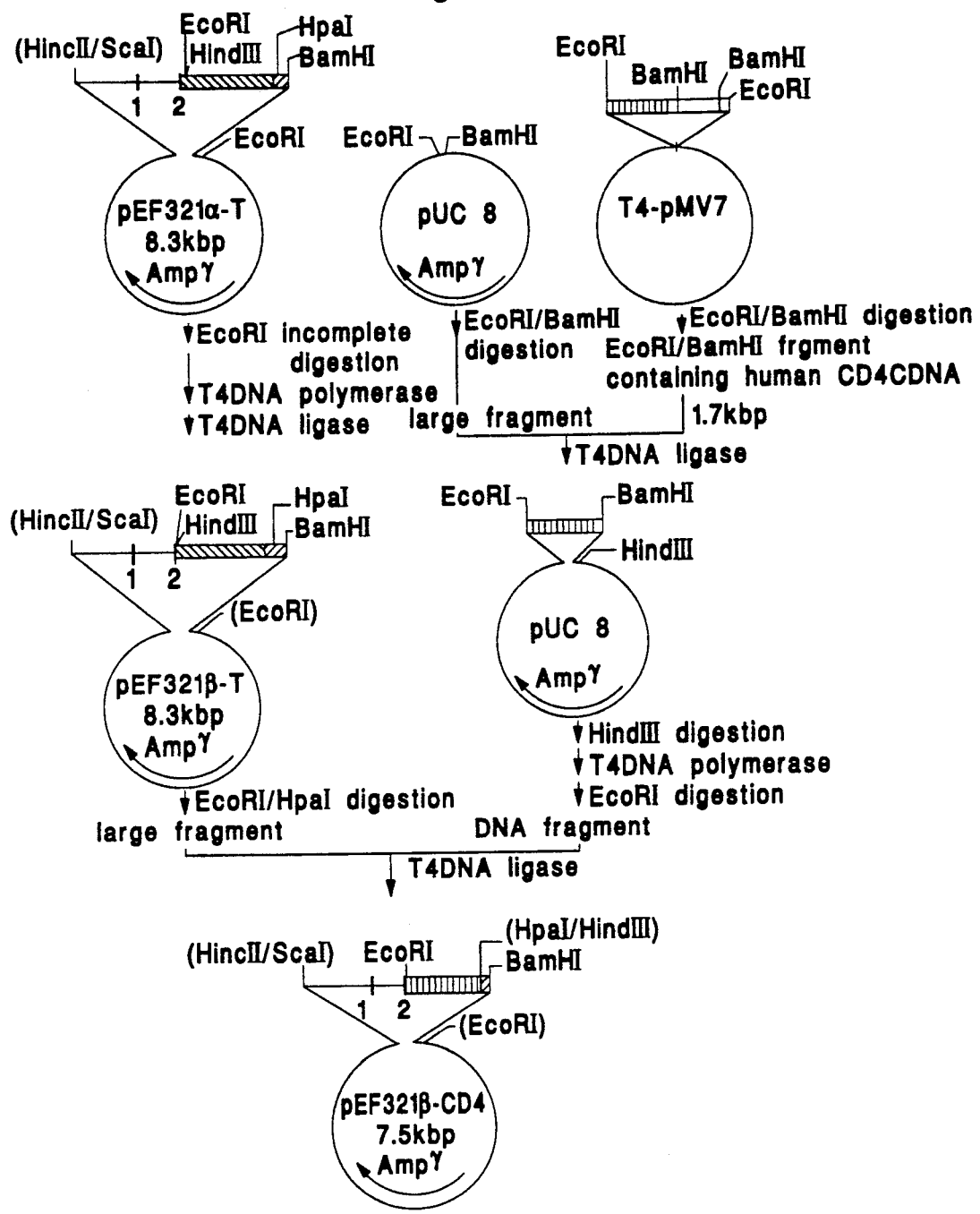
FIG. 9 is a flow diagram for the construction of plasmid pEF321β-CD4.

Construction of Human CD4 cDNA Expression Plasmid Containing Promoter Region of Human EF-1α Gene A flow diagram for the construction of this plasmid is shown in FIG. 9. Human CD4 cDNA (about 1.7 kilo base pairs) was cut out as an EcoRI-BamHI fragment from plasmid T4-pMV7 containing human CD4 cDNA (P. J. Maddon et al. (1986) *Cell* 47:333) and inserted into plasmid pUC 8. The resulted plasmid was digested with HindIII, smooth-ended using T4 DNA polymerase and again digested with EcoRI, in order to isolate a CD4 cDNA fragment. A plasmid pEF321β-T was obtained by eliminating pUC 119-originated EcoRI recognition site from the plasmid pEF321α-T prepared in Example 3 by using the same method described in Example 3-(1). A plasmid, named pEF321β-CD4, was constructed by digesting the plasmid pEF321β-T with EcoRI and HpaI and then ligating a large fragment isolated from the digested fragments with the above-described human CD4 cDNA fragment using T4 DNA ligase.

EXAMPLE 5

Expression of CAT Gene

Expression efficiencies of four expression plasmids containing promoter region of human EF-1α gene, pEF220-CAT, pEF223-CAT, pEF204-CAT and pEF321-CAT, were compared with those of other expression plasmids pSV2-CAT and pSRα-CAT (kindly provided by Dr. Takebe at National Institute of Health (Japan)).

(1) Transfection of Expression Plasmids onto Various Cell Lines

The following shows cell lines used in this experiment and conditions for the culturing of each cell line, including medium, cell density of the inoculum (the number of cells per 10 cm² plate medium) and culture time.
  a) CHO-K1 (Chinese hamster ovary cell, ATCC CCL61) 10% FCS-containing Ham's F12 medium $1.2 \times 10^6$ cells, 48 h
  b) IMR-32 (human neuroblast cell, ATCC CCL127) 10% FCS-containing DMEM medium $2.0 \times 10^6$ cells, 48 h
  c) 3Y1 (rat fibroblast cell) 8% FCS-containing DMEM medium $2.0 \times 10^6$ cells, 24 h
  d) CV-1 (African green monkey kidney cell, ATCC CCL70) 8% FCS-containing DMEM medium $2.0 \times 10^6$ cells, 24 h
  e) COS-1 (African green monkey kidney cell transformed by SV40, ATCC CRL1650) 8% FCS-containing DMEM medium $2.0 \times 10^6$ cells, 24 h
  f) T22 (monkey kidney cell transformed by SV40) 8% FCS-containing DMEM medium $2.0 \times 10^6$ cells, 24 h
  g) BrA2-227 (rat brain cell line immortalized by SV40 mutant T antigen A2) 8% FCS-containing DMEM medium $2.0 \times 10^6$ cells, 24 h
  h) BrA2-SS (rat brain cell line immortalized by SV40 mutant T antigen A2) 8% FCS-containing DMEM medium $2.0 \times 10^6$ cells, 24 h
  i) JTC-16P3 (rat hepatoma cell, JCRB 0714) 1% FCS-containing DM-160AU medium About 50% confluent, 48 h
  j) NY (human oesteosarcoma cell, JCRB 0614) 8% FCS-containing MEM medium $2.0 \times 10^6$ cells, 72 h
  k) MT-1 (human T cell leukemia cell, JCRβ 0063) 10% FCS-containing RPMI 1640 medium An aliquot of cell suspension containing $2 \times 10^6$ cells was used Each cell line was cultured under these conditions prior to the addition of plasmid DNA, and the culture medium was renewed about one hour before the addition of plasmid DNA.

A 0.45 ml portion of solution containing 10 to 20 μg of each plasmid DNA was mixed with 50 μl of 2.5M CaCl$_2$, stirred while 0.5 ml of 2×HBS (280 mM NaCl/50 mM HEPES/2.8 mM Na$_2$HPO$_4$, pH 7.05) was dripped and then maintained at room temperature for 10 min. The DNA precipitate thus obtained was applied to the above-described medium containing cultured cells and incubated for 6 h. The cells were washed with about 10 ml of PBS and treated with 20% DMSO/-medium for 3 min in order to obtain transfectants. The transfectants thus obtained were washed with PBS, suspended in the medium and stored at 37° C. in the presence of 5% CO$_2$.

(2) CAT Assay

CAT assay was performed in accordance with the method of C. M. Gorman et al. (*Mol. Cell. Biol.* 2:1044; 1982). Each cell line was cultured at 37° C. for 48 h in the presence of 5% CO$_2$, and the cultured cells were rinsed twice with PBS and harvested by centrifugation at 1000 rpm for 3 min. The cells were suspended in 200 μl of 0.25M Tris-HCl (pH 7.8), subjected to three cycles of freeze-thaw and then disrupted by sonication. The sonicated suspension was centrifuged at 15,000 rpm for 15 min at 40° C., and an aliquot of the resulting supernatant was assayed for protein content in accordance with the method of Bradford et al. (*Anal. Biochem.* 72:248; 1976).

Based on the result of the protein assay, a supernatant which seemed to have the protein content of about 150 μg was selected, with the exception of 2 μg, 18 μg, 6 μg, 41 μg and 760 μg in the case of CHO-K1, NY, JTC-16P3, MT-1 and IMR-32, respectively. An aliquot of the supernatant thus selected was mixed in a final volume of 238 μl, with 0.2 μCi of [$^{14}$C] chloramphenicol (Amersham)/1 mM acetyl-CoA/0.25M Tris-HCl (pH 7.8). After incubation at 37° C. for 2 h (30 min in the case of CHO-K1 and NY and 40 min in JTC-16P3), the contents of the reaction solution were extracted with ethyl acetate and then solidified by evaporation. The solid was dissolved again in 15 μl of ethyl acetate and spotted on a silica gel thin layer plate (20 cm in length, a product of Merck & Company, Inc.). The chromatography was performed using chloroform/methanol (95:5) system as the development solvent. The plate was dried when the solvent reached a level 13 cm from the upper end. An X-ray film was then laid on top of the thin layer plate and kept for 18 to 20 h (3 days in the case of MT-1) to take an autoradiograph.

The amount of CAT expressed by each transfectant was estimated based on the ratio of acetylated [$^{14}$C] chloramphenicol. In addition, the radioactivity on the thin layer plate was directly counted by using a Radio Analytic Labeling System (trade name of a product of AMBIS System Inc.) as a quantitative measuring method.

As a typical example, results of the measurement of the expression efficiency of CAT gene in IMR-32 cells by using the Radio Analytic Labeling System are shown in FIG. 10. Each number shown in the figure indicates the degree of the radioactivity of [$^{14}$C] chloramphenicol or acetylated [$^{14}$C] chloramphenicol. The ratio of the acetylated [$^{14}$C] chloramphenicol can be expressed as (acetylated product) (acetylated product+unchanged material). On the basis of these results, it was found that all of the four expression plasmids containing promoter region of human EF-1α gene had high expression efficiency, even in the case of human neuroblastoma cell (IMR-32) in which the efficiency of SV40 promoter-containing expression plasmid was remarkably low. In IMR-32 cell, the exon 2-containing pEF321-CAT was about 100 fold and about 10 fold more higher in the expression efficiency compared to pSV2-CAT and pSRα-CAT, respectively.

The ratio of acetylated products by each expression plasmid is summarized in Table 1.

TABLE 1

| Comparison of expression efficiencies of CAT gene. | | | | | |
|---|---|---|---|---|---|
| Examples | | | Comparative Examples | | |
| pEF220-CAT | pEF223-CAT | pEF204-CAT | pEF321-CAT | pSV2-CAT | pSRα-CAT |

| | pEF220-CAT | pEF223-CAT | pEF204-CAT | pEF321-CAT | pSV2-CAT | pSRα-CAT |
|---|---|---|---|---|---|---|
| IMR-32 | 30 | 95 | 95 | 97 | 1 | 9 |
| CHO-K1 | 3 | 12 | 17 | 26 | 14 | |
| 3Y1 | | | 66 | 95 | 6 | 94 |
| JTC-16P3 | | | 10 | 26 | 7 | 33 |
| NY | | | 4 | 9 | 2 | 6 |
| MT-1 | | | 1 | 5 | 1 | 1 |
| BrA2-227 | | | | 39 | 8 | 35 |
| BrA2-SS | | | | 96 | 47 | 93 |
| CV-1 | | | | 84 | 5 | |
| COS-1 | | | | 98 | 34 | |
| T22 | | | | 99 | 75 | |

Blanks: not measured.

Comparison of expression efficiencies of the four expression plasmids containing promoter region of human EF-1α gene in CHO-K1 and IMR-32 cells revealed the following order of expression level: pEF321-CAT>pEF204-CAT, pEF223-CAT>pEF220-CAT. In addition, the expression efficiency of the plasmid pEF321-CAT which showed the highest expression efficiency in both CHO-K1 and IMR-32 cells was similar to or higher than those of the two SV40 promoter-containing plasmids in all tested cell lines.

EXAMPLE 6

Expression of SV40 T Antigen Gene

Figure 11:
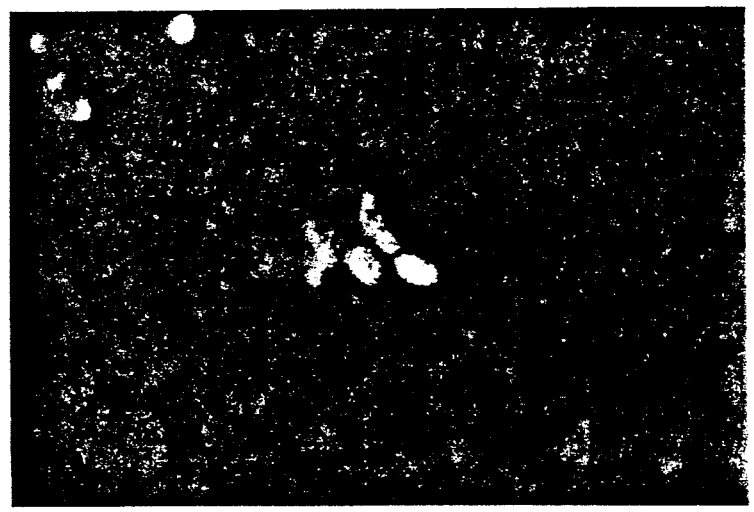
FIGS. 11 to 15 are immunofluorescence microphotographs showing the distribution of expressed proteins within cells. In particular.
Figure 12:
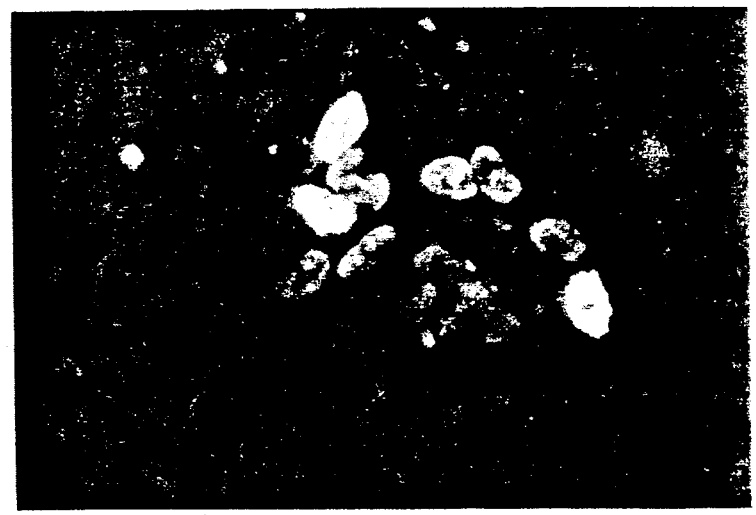

Transfection of plasmids pEF204α-T, pEF321α-T and pMT1 on to IMR-32 cells were performed in accordance with the procedure described in Example 5-(1). At 48 hours after the transfection reaction, the cells were fixed by using a mixture of ethanol and acetone (1:1) at −20° C. for 18 min and subjected to the immunofluorescence assay. As the first antibody, a hamster antiserum specific for SV40 T antigen was prepared as follows. About 2×10$^6$ SV40 transformant cells were inoculated subcutaneously to a three- to four-month-old hamster and the individual was reared further (generally for 2 to 6 months) until the formation of tumor was completed. After fasting for one day, whole blood of the hamster was collected in order to isolate an antiserum preparation. The fixed cells described above were incubated with the antiserum thus obtained at 37° C. for 1 h. The cells were then washed with PBS- and incubated with FITC-labeled rabbit anti-hamster IgG (a product of FUJIREBIO Inc.) at 37° C. for 1 h. After washing the resulting cells with PBS-, the fluorescence was measured using a reflected light fluorescence microscope (Mofel BH2, Olympus Optical Co., Ltd.). As the result, the expression of T antigen was detected in the cells transfected with plasmids pEF204α-T and pEF321α-T as shown in FIGS. 11 and 12, but not in the cells transfected with plasmid pMT1.

EXAMPLE 7

Measurement of the Stability of Expression Plasmids

Transfection of plasmids pEF204α-T, pEF321α-T and pMT1 on to 3Y1 cells were performed in the same manner as described in Example 6. At 24 hours after the transfection culturing, the cells were replated using a trypsin solution (0.05% trypsin/PBS) and cultured further at 37° C. for one month in the presence of 5% $CO_2$.

As the result, all three groups of the cells transfected with pEF204α-T, pEF321α-T and pMT1 plasmid DNAs formed many high density foci. The number of focus was high in the cells transfected with plasmid pEF204α-T or plasmid pEF321α-T compared to the cells transfected with pMT1 plasmid.

Figure 13:
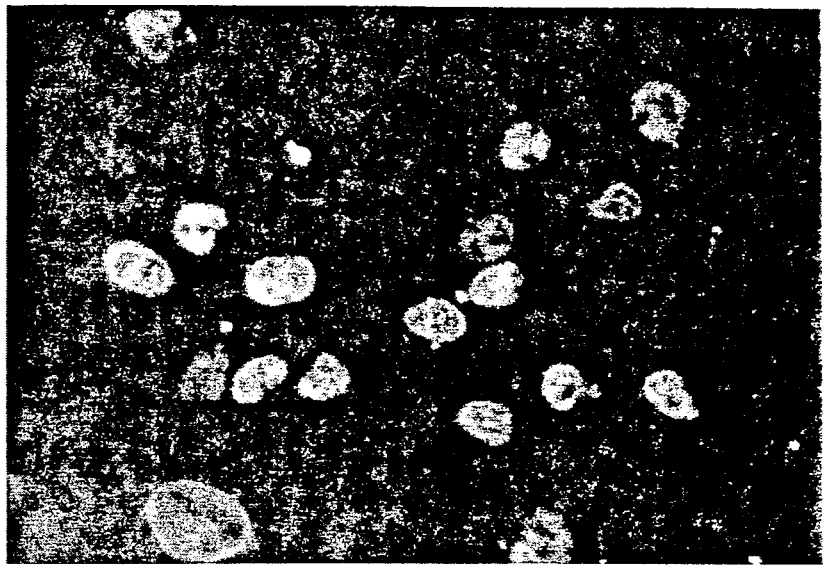
Figure 14:
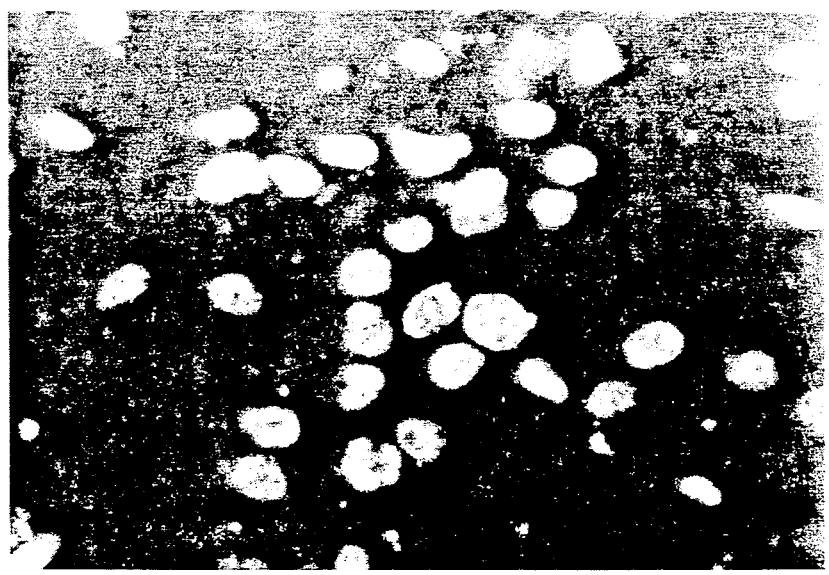

Single focus was isolated from each group of the cells, treated with the trypsin solution, replated, and then subjected to the immunofluorescence assay in accordance with the procedure described in Example 6. As shown in FIGS. 13 and 14, T antigen was detected in the cell nucleus of the cells transfected with pEF204α-T or pEF321α-T plasmid DNA, which indicated that these plasmid DNAs were maintained stably for one month in the cells.

EXAMPLE 8

Expression of Human CD4 Gene

Plasmid pEF321β-CD4 was transfected on to CHO-K1 cell in accordance with the procedure described in Example 6. Immunofluorescence assay was performed according to Example 6 using a mouse monoclonal antibody specific for human CD4 (OKT4, a product of Ortho Diagnostic Systems K. K.) as the first antibody and an FITC-labeled rabbit anti-mouse IgG (a product of Medical & Biological Laboratories Co., Ltd.) as the second antibody.

Figure 15:

Since the human CD4 protein was detected in the cellular membrane of the transfected cells as shown in FIG. 15, expression of human CD4 by the plasmid pEF321β-CD4 in CHO-K1 cell was confirmed.

As have been described in detail in the foregoing, the present inventors have developed a novel DNA fragment containing the promoter region of human polypeptide chain elongation factor-1α and new expression plasmids containing said DNA fragment having higher applicability to a wider range of host cells with higher expression capacity compared to the applicability and expression capacity of any expression plasmid containing commonly used promoters, such as SV40 early promoter. The present inventors have also revealed the structure described above of said DNA fragment by determining its base sequence. Since these expression plasmids of the present invention were able to be maintained stably in certain host cells at least for one month, application of said expression plasmids may render possible the production of various kinds of useful physiologically active substances efficiently for a long period using a wide range of mammalian cells as the host.

EXAMPLE 9

Construction of Expression Plasmids (1) Plasmid pEF-SV-CSF

Figure 16:
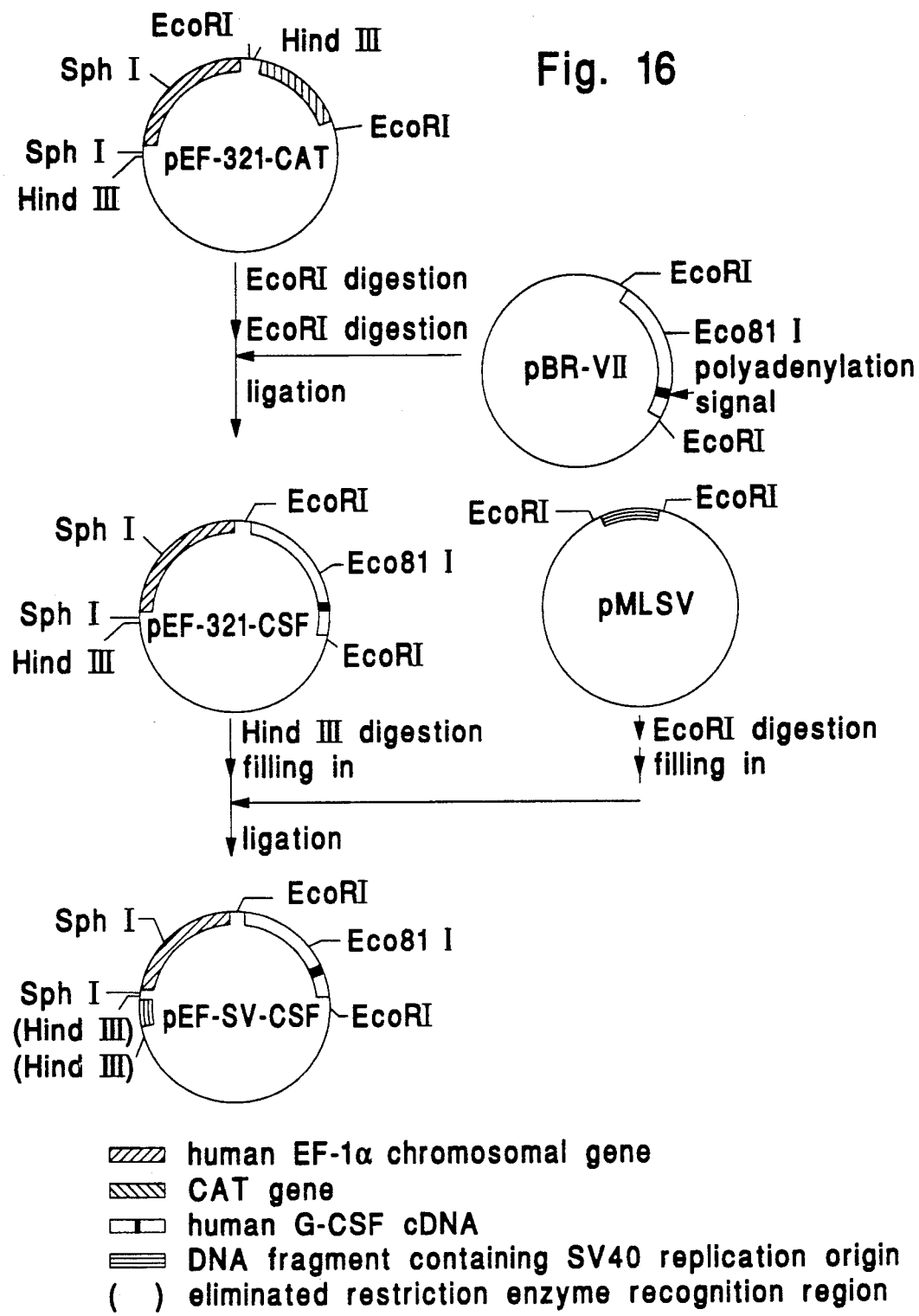
FIG. 16 is a diagram of the construction of an expression plasmid pEF-SV-CSF.

This plasmid was constructed in the following manner. Basic process for its construction is shown in FIG. 16.

An EcoRI-EcoRI cDNA fragment containing CAT gene was removed from an expression plasmid pEF-321-CAT which has been constructed by D. W. Kim et al. (*Gene* 91:217; 1990). An EcoRI-EcoRI DNA fragment containing G-CSF cDNA was cut out from plasmid pBR-VII and ligated with the above EcoRI-EcoRI large fragment to obtain plasmid pEF-321-CSF. Thereafter, an EcoRI-EcoRI DNA fragment containing a 311 bp DNA fragment in which a SV40 replication origin is contained was inserted into the HindII recognition site located upstream of EF-1α promoter region in the thus prepared plasmid pEF-321-CSF to yield the title expression plasmid pEF-SV-CSF.

(2) Plasmid pEF-BOS

The process for the construction of this plasmid is generally illustrated in FIG. 17. From the G-CSF-containing cDNA moiety in the plasmid pEF-321-CSF prepared in Example 9-(1), a region encoding G-CSF was removed by cutting out its upstream portion starting from the Eco81T recognition site. At the same time, a XbaI linker was inserted into the EcoRI recognition site located between the EF-1α promoter region and the G-CSF polyadenylation signal. In this way, a plasmid containing a XbaI recognition site was obtained. Into the XbaI recognition site of the thus constructed new plasmid was inserted a 451 bp stuffer gene of plasmid CDM8 (Seed, B: *Nature* 329:840; 1987).

Next a SphI-SphI DNA fragment which is located in the upstream portion of the DNA fragment including the EF-1α promoter region in the thus obtained plasmid was removed and replaced by an EcoRI-EcoRI DNA fragment containing a 311 bp DNA fragment including SV40 replication origin in the same manner as in Example 9-(1). Thereafter the BstXI recognition site in the nucleotide sequence containing EF-1α promoter region was removed by deleting a nucleotide sequence GCCC to yield the title expression plasmid pEF-BOS.

EXAMPLE 10

Production of Human G-CSF in COS Cells

Human G-CSF cDNA was inserted into BstXI site of pEF-BOS or CDM8, or into BamHI site of pKCR vector containing SV40 early promoter (O'Hare, K., Benoist, C. and Breathnach, R. (1981) *Proc. Natl. Acad. Sci. USA* 78:1527–1531). As shown in Table 2, when these plasmids were transfected into COS cells by DEAE-dextran/chloroquine method, the construct in pEF-BOS directed the synthesis of human G-CSF about 20 times more efficiently than the construct in CDM8, and 50–200 times more efficiently than the construct in pKCR.

G-CSF activities were titrated by a biological assay with mouse interleukin-3 (IL-3)-dependent cell line NFS-60, which can grow in the presence of G-CSF. Since the number of surviving NFS-60 cells after addition of a sample that contains human G-CSF correlates to the sum of DNA synthesis in the cells, a half-maximum value of [$^3$thymidine incorporation into the cells indicates the G-CSF activity of the sample.

TABLE 2

| Production of human G-CSF in COS cells | | |
|---|---|---|
| Vector | G-CSF activity in medium$^a$ (units$^b$/ml) | |
| pEF-BOS | 33,000 | 12,000 |
| CDM8 | 1,600 | 1,200 |
| PKCR | 160 | 160 |

$^a$At 72 hrs. post transfection. the G-CSF activity in the medium was assayed.
$^b$1 unit of the activity corresponds to about 62 pg of human G-CSF.

Figure 18:
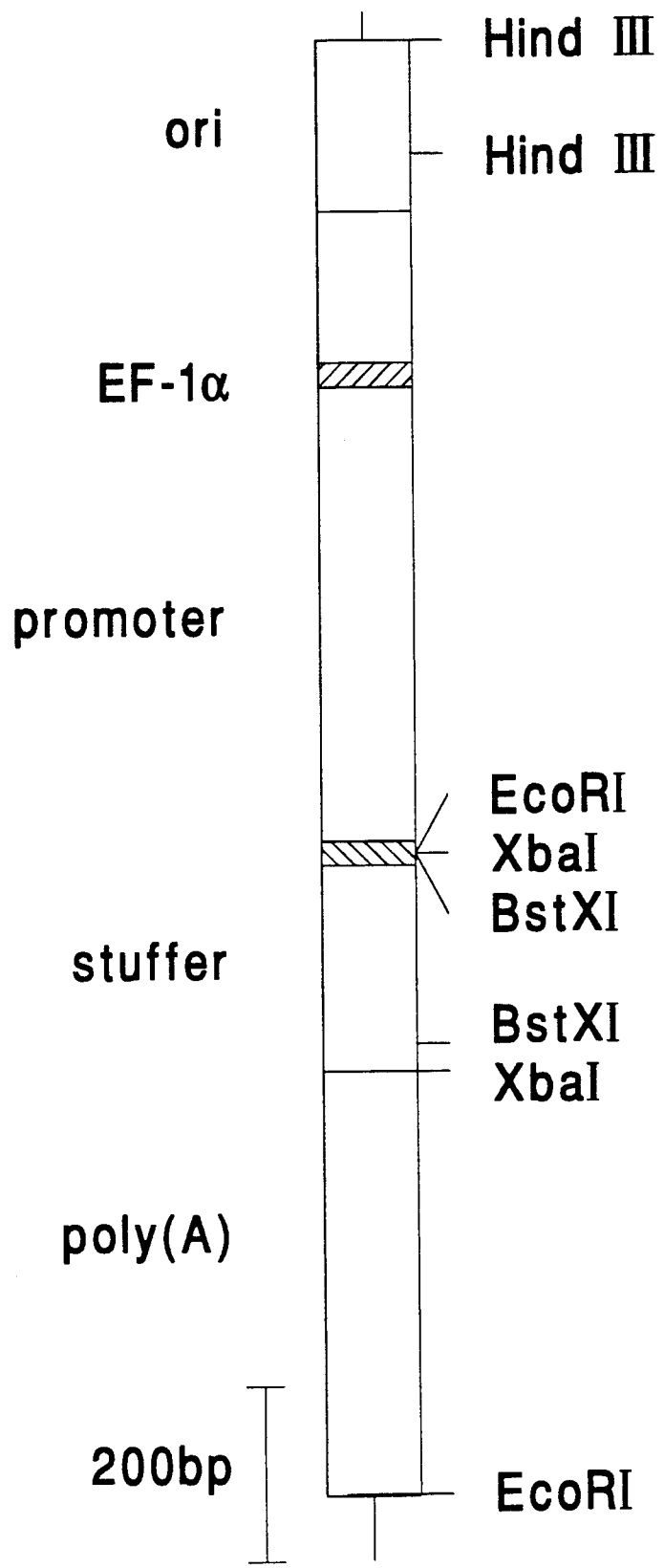
FIG. 18 is a diagram of the structure of pEF-BOS.

As shown in FIG. 18, pEF-BOS carries the SV40 replication origin (311 bp of EcoRII fragment), the promoter region of human EF-1α chromosomal gene (1.2 kb), the stuffer fragment (451 bp) from CDM8 vector and polyadenylation signal from human G-CSF cDNA (700 bp Eco81I-EcoRI DNA fragment) (Nagata et al. (1986) *Nature* 319: 415–418) in HindIII-EcoRI site of pUC119. The promoter region of EF-1α gene is from nucleotide position 373 to 1561, as shown in the SEQ ID NO:4, which includes 203 bp of the 5' flanking region, 33 bp of the first exon, 939 bp of the first intron and 10 bp of the part of the second exon located at 20 bp upstream of the ATG initiation codon. The size of pEF-BOS is 5.8 kb, and the cDNA to be expressed can be inserted at BstXI site using a BstXI adapter, or XbaI site using a XbaI linker.

EXAMPLE 11

Effect of SV40 Replication Origin on the Expression in COS Cells

The plasmids pEF-BOS, pEF-SV and pEF-321 were compared to terms of their efficiencies in the expression of human G-CSF cDNA in COS cells, by the method used in example 10. Plasmid pEF-SV contains a EF-1α promoter region of 2.5 kilo base pairs and SV40 replication origin, while plasmid pEF-321 contains the EF-1α promoter region of 2.5 kilo base pairs, but no SV40 replication origin. As summarized in Table 3, both plasmids containing the SV40 replication origin, pEF-SV and pEF-BOS, exhibited expression of the G-CSF gene at a level more than ten times higher than expression by plasmid pEF-321 which contained no SV40 replication origin.

TABLE 3

| Vector | EF-1α promoter region | SV40 replication origin | C-CSF activity in medium[a] (units[b]/ml) |
|---|---|---|---|
| pEF-321 | 2.5 Kbp | − | 700 |
| pEF-SV | 2.5 Kbp | + | 10,000 |
| pEF-BOS | 1.2 Kbp | + | 12,000 |

[a] At 72 hrs post transfection, G-CSF activity in the medium was assayed.
[b] One unit of the activity corresponds to about 62 pg of human G-CSF.

EXAMPLE 12

Effect of the Inventive Plasmids in Various Cell Lines

When a CAT gene was inserted into pEF-BOS, the CAT activities observed with pEF-BOS-CAT were 1.5–50 times higher than that of pSV2-CAT or pRSV-CAT after introduction into various cell lines including murine L929, human HeLa, CHU-2 and simian COS cells (Table 4). The pEF-BOS vector, therefore, will be used to produce a large amount of growth factors and proteins in mammalian cells, and to express a high level of anti-sense RNA. Furthermore, the pEF-BOS-CAT will be an ideal positive control for CAT assay in various cell types.

TABLE 4

| | Promoter activities in various cells | | | |
|---|---|---|---|---|
| | Relative CAT activities[a] | | | |
| Vector | L929 | HeLa | CHU-2 | COS |
| pSV2 | 2.0 | 74.3 | 82.7 | 10.2 |
| pRSV | 8.0 | 8.5 | 19.2 | 22.5 |
| pEF-BOS | 100 | 100 | 100 | 100 |
| CDM8 | n.t.[b] | n.t. | n.t. | 25.4 |

[a] CAT activities are presented as a percentage of that of the pEF-BOS
[b] n.t., not tested.

What is claimed is:

1. An essentially pure DNA fragment which is represented by the following sequence (SEQ ID NO:4):

```
373    CGTGAGGC
              TCCGGTGCCCGTCAGTGGGC     400
AGAGCGCACATCGCCCACAG
              TCCCCGAGAAGTTGGGGGGA     440
GGGGTCGGCAATTGAACCGG
              TGCCTAGAGAAGGTGGCGCG     480
GGGTAAACTGGGAAAGTGAT
              GTCGTGTACTGGCTCCGCCT     520
TTTTCCCGAGGGTGGGGGAG
              AACCGTATATAAGTGCAGTA     560
GTCGCCGTGAACGTTCTTTT
              TCGCAACGGGTTTGCCGCCA     600
GAACACAGGTAAGTGCCGTG
              TGTGGTTCCCGCGGGCCTGG     640
CCTCTTTACGGGTTATGGCC
              CTTGCGTGCCTTGAATTACT     680
TCCACGCCCCTGGCTGCAGT
              ACGTGATTCTTGATCCCGAG     720
CTTCGGGTTGGAAGTGGGTG
              GGAGAGTTCGAGGCCTTGCG     760
CTTAAGGAGCCCCTTCGCCT
              CGTGCTTGAGTTGAGGCCTG     800
GCCTGGGCGCTGGGGCCGCC
              GCGTGCGAATCTGGTGGCAC     840
CTTCGCGCCTGTCTCGCTGC
              TTTCGATAAGTCTCTAGCCA     880
TTTAAAATTTTTGATGACCT
              GCTGCGACGCTTTTTTTCTG     920
GCAAGATAGTCTTGTAAATG
              CGGGCCAAGATCTGCACACT     960
GGTATTTCGGTTTTTGGGGC
              CGCGGGCGGCGACGGGGCCC     1000
GTGCGTCCCAGCGCACATGT
              TCGGCGAGGCGGGGCCTGCG     1040
AGCGCGGCCACCGAGAATCG
              GACGGGGGTAGTCTCAAGCT     1080
GGCCGGCCTGCTCTGGTGCC
              TGGCCTCGCGCCGCCGTGTA     1120
TCGCCCCGCCCTGGGCGGCA
              AGGCTGGCCCGGTCGGCACC     1160
AGTTGCGTGAGCGGAAAGCT
              GGCCGCTTCCCGGCCCTGCT     1200
GCAGGGAGCTCAAAATGGAG
              GACGCGGCGCTCGGGAGAGC     1240
GGGCGGGTGAGTCACCCACA
              CAAAGGAAAAGGGCCTTTCC     1480
GTCCTCAGCCGTCGCTTCAT
              GTGACTCCACGGAGTACCGG     1320
```

```
GCGCCGTCCAGGCACCTCGA
            TTAGTTCTCGAGCTTTTGGA  1360
GTACGTCGTCTTTAGGTTGG
            GGGGAGGGGTTTTATGCGAT  1400
GGAGTTTCCCCACACTGAGT
            GGGTGGAGACTGAAGTTAGG  1440
CCAGCTTGGCACTTGATGTA
            ATTCTCCTTGGAATTTGCCC  1480
TTTTTGAGTTTGGATCTTGG
            TTCATTCTCAAGCCTCAGAC  1520
AGTGGTTCAAAGTTTTTTTC
            TTCCATTTCAGGTGTCGTGA  1560
A           1561.
```

(SEQ ID No: 4)

2. An essentially pure DNA fragment which is represented by the following sequence (SEQ ID NO:5):

```
373     CGTGAGGCTCCGGTGCCCGTCAGTGGGC    400
        AGAGCGCACATCGCCCACAGTCCCCGAGAAGTTGGGGGGA    440
        GGGGTCGGCAATTGAACCGGTGCCTAGAGAAGGTGGCGCG    480
        GGGTAAACTGGGAAAGTGATGTCGTGTACTGGCTCCGCCT    520
        TTTTCCCGAGGGTGGGGGAGAACCGTATATAAGTGCAGTA    560
        GTCGCCGTGAACGTTCTTTTTCGCAACGGGTTTGCCGCCA    600
        GAACACAGGTAAGTGCCGTGTGTGGTTCCCGCGGGCCTGG    640
        CCTCTTTACGGGTTATGGCCCTTGCGTGCCTTGAATTACT    680
        TCCACCTGGCTGCAGTACGTGATTCTTGATCCCGAG       720
        CTTCGGGTTGGAAGTGGGTGGGAGAGTTCGAGGCCTTGCG   760
        CTTAAGGAGCCCCTTCGCCTCGTGCTTGAGTTGAGGCCTG   800
        GCCTGGGCGCTGGGGCCGCCGCGTGCGAATCTGGTGGCAC   840
        CTTCGCGCCTGTCTCGCTGCTTTCGATAAGTCTCTAGCCA   880
        TTTAAAATTTTTGATGACCTGCTGCGACGCTTTTTTTCTG   920
        GCAAGATAGTCTTGTAAATGCGGGCCAAGATCTGCACACT   960
        GGTATTTCGGTTTTTGGGGCCGCGGGCGGCGACGGGGCCC   1000
        GTGCGTCCCAGCGCACATGTTCGGCGAGGCGGGGCCTGCG   1040
        AGCGCGGCCACCGAGAATCGGACGGGGGTAGTCTCAAGCT   1080
        GGCCGGCCTGCTCTGGTGCCTGGCCTCGCGCCGCCGTGTA   1120
        TCGCCCCGCCCTGGGCGGCAAGGCTGGCCCGGTCGGCACC   1160
        AGTTGCGTGAGCGGAAAGATGGCCGCTTCCCGGCCCTGCT   1200
        GCAGGGAGCTCAAAATGGAGGACGCGGCGCTCGGGAGAGC   1240
        GGGCGGGTGAGTCACCCACACAAAGGAAAAGGGCCTTTCC   1480
        GTCCTCAGCCGTCGCTTCATGTGACTCCACGGAGTACCGG   1320
        GCGCCGTCCAGGCACCTCGATTAGTTCTCGAGCTTTTGGA   1360
        GTACGTCGTCTTTAGGTTGGGGGGAGGGGTTTTATGCGAT   1400
        GGAGTTTCCCCACACTGAGTGGGTGGAGACTGAAGTTAGG   1440
        CCAGCTTGGCACTTGATGTAATTCTCCTTGGAATTTGCCC   1480
        TTTTTGAGTTTGGATCTTGGTTCATTCTCAAGCCTCAGAC   1520
        AGTGGTTCAAAGTTTTTTTCTTCCATTTCAGGTGTCGTGA   1560
```

A    1561.

-continued
(SEQ ID No:5)

3. An expression plasmid containing the DNA fragment according to claim 1.

4. An expression plasmid containing a DNA fragment according to claim 2.

5. An expression plasmid according to claim 4, wherein the plasmid is pEF-BOS.

6. An expression plasmid containing a SV40 replication origin and at least one fragment according to claim 1.

7. An expression plasmid containing a SV40 replication origin and at least one fragment according to claim 2.

* * * * *